US008864680B2

(12) United States Patent
Videbæk et al.

(10) Patent No.: US 8,864,680 B2
(45) Date of Patent: Oct. 21, 2014

(54) TRANSPORT SYSTEM FOR BIOPSY DEVICE

(75) Inventors: Karsten Videbæk, Roskilde (DK); Martin Bondo Jørgensen, Vaerløse (DK); Lasse Danborg, Glostrup (DK); Lasse G. Staal, Stenløse (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 335 days.

(21) Appl. No.: 11/631,702

(22) PCT Filed: Jul. 8, 2005

(86) PCT No.: PCT/DK2005/000484
§ 371 (c)(1),
(2), (4) Date: Nov. 26, 2007

(87) PCT Pub. No.: WO2006/005344
PCT Pub. Date: Jan. 19, 2006

(65) Prior Publication Data
US 2008/0287826 A1    Nov. 20, 2008

Related U.S. Application Data

(60) Provisional application No. 60/586,290, filed on Jul. 9, 2004, provisional application No. 60/625,127, filed on Nov. 5, 2004, provisional application No. 60/625,128, filed on Nov. 5, 2004.

(51) Int. Cl.
*A61B 10/02* (2006.01)
(52) U.S. Cl.
CPC ......... *A61B 10/0275* (2013.01); *A61B 10/0283* (2013.01); *A61B 2010/0208* (2013.01); *A61B 2010/0225* (2013.01)
USPC .......................................... 600/567; 600/566

(58) Field of Classification Search
USPC ........................... 600/562–568; 606/167, 170
See application file for complete search history.

(56) References Cited

U.S. PATENT DOCUMENTS

| 737,293 | A |  | 8/1903 | Summerfeldt |
|---|---|---|---|---|
| 1,585,934 | A |  | 5/1926 | Muir |
| 1,663,761 | A |  | 3/1928 | Johnson |
| 2,953,934 | A | * | 9/1960 | Sundt .......................... 74/424.74 |

(Continued)

FOREIGN PATENT DOCUMENTS

| DE | 3924291 A1 | 7/1989 |
|---|---|---|
| DE | 4041614 C1 | 10/1992 |

(Continued)

*Primary Examiner* — Rene Towa
*Assistant Examiner* — Emily Lloyd

(57) ABSTRACT

A biopsy device for harvesting tissue samples from a body of a living being, e.g. in percutaneous aspiration biopsy, includes an outer needle and a sample-receiving device for receiving a severed tissue sample, the sample-receiving device being movable in the hollow needle. The device includes a transport device for moving the sample-receiving device in the hollow needle, the transport device comprising a bendable elongate element, such as a steel wire, a toothed wire made from e.g. a plastics material or a Bowden cable capable of pushing and pulling the sample-receiving device in distal and proximal directions, respectively. A coiling device is provided for the bendable elongate element. The bendable elongate element and the coiling device may be included in a disposable unit, which is attachable to a hand-held unit including a motor for driving the transport device. Orientation means are provided for appropriately orienting the sample-receiving device with respect to the hollow needle.

26 Claims, 28 Drawing Sheets

(56) References Cited

U.S. PATENT DOCUMENTS

| | | | |
|---|---|---|---|
| 3,019,733 A | 2/1962 | Braid | |
| 3,224,434 A | 12/1965 | Molomut et al. | |
| 3,289,669 A | 12/1966 | Dwyer et al. | |
| 3,477,423 A | 11/1969 | Griffith | |
| 3,512,519 A | 5/1970 | Hall | |
| 3,561,429 A | 2/1971 | Jewett | |
| 3,565,074 A | 2/1971 | Foti | |
| 3,606,878 A | 9/1971 | Kellogg | |
| 3,727,602 A | 4/1973 | Hyden et al. | 128/278 |
| 3,732,858 A | 5/1973 | Banko | |
| 3,785,380 A | 1/1974 | Brumfield | |
| 3,800,783 A | 4/1974 | Jamshidi | |
| 3,844,272 A | 10/1974 | Banko | 128/305 |
| 3,882,849 A | 5/1975 | Jamshidi | |
| 3,889,682 A | 6/1975 | Denis et al. | |
| 4,275,730 A | 6/1981 | Hussein | |
| 4,282,884 A * | 8/1981 | Boebel | 600/564 |
| 4,306,570 A | 12/1981 | Matthews | |
| 4,354,092 A | 10/1982 | Manabe et al. | |
| 4,393,879 A | 7/1983 | Milgrom | |
| 4,445,509 A | 5/1984 | Auth | |
| 4,490,137 A | 12/1984 | Moukheibir | |
| 4,549,554 A | 10/1985 | Markham | |
| 4,577,629 A | 3/1986 | Martinez | |
| 4,589,414 A | 5/1986 | Yoshida et al. | |
| 4,603,694 A | 8/1986 | Wheeler | |
| 4,605,011 A | 8/1986 | Naslund | |
| 4,616,215 A | 10/1986 | Maddalena | |
| 4,617,430 A | 10/1986 | Bryant | |
| 4,620,539 A | 11/1986 | Andrews et al. | |
| 4,643,197 A | 2/1987 | Greene et al. | |
| 4,645,153 A | 2/1987 | Granzow et al. | |
| 4,678,459 A | 7/1987 | Onik et al. | |
| 4,696,298 A | 9/1987 | Higgins et al. | |
| 4,702,260 A | 10/1987 | Wang | |
| 4,706,687 A | 11/1987 | Rogers | |
| 4,776,346 A | 10/1988 | Beraha et al. | |
| 4,792,327 A | 12/1988 | Swartz | |
| 4,832,044 A | 5/1989 | Garg | |
| 4,844,087 A | 7/1989 | Garg | |
| 4,850,354 A | 7/1989 | McGurk-Burleson et al. | |
| 4,893,635 A | 1/1990 | de Groot et al. | |
| 4,907,598 A | 3/1990 | Bauer | |
| 33,258 A | 7/1990 | Onik et al. | |
| RE33,258 E | 7/1990 | Onik et al. | |
| 4,940,061 A | 7/1990 | Terwilliger et al. | |
| 4,952,817 A | 8/1990 | Bolan et al. | |
| 4,958,625 A | 9/1990 | Bates et al. | |
| 4,967,762 A | 11/1990 | DeVries | |
| 4,986,278 A | 1/1991 | Ravid et al. | |
| 4,986,279 A | 1/1991 | O'Neill | |
| 4,986,807 A | 1/1991 | Farr | |
| 4,989,614 A | 2/1991 | Dejter, Jr. et al. | |
| 5,025,797 A | 6/1991 | Baran | |
| 5,048,538 A | 9/1991 | Terwilliger et al. | |
| 5,057,822 A | 10/1991 | Hoffman | |
| 5,078,603 A | 1/1992 | Cohen | |
| 5,125,413 A | 6/1992 | Baran | |
| 5,138,245 A | 8/1992 | Mattinger et al. | |
| 5,146,921 A | 9/1992 | Terwilliger et al. | |
| 5,156,160 A | 10/1992 | Bennett | |
| 5,158,528 A | 10/1992 | Walker et al. | |
| 5,172,702 A | 12/1992 | Leigh et al. | |
| 5,176,628 A | 1/1993 | Charles et al. | |
| 5,223,012 A | 6/1993 | Best et al. | |
| 5,225,763 A | 7/1993 | Krohn et al. | |
| 5,234,000 A | 8/1993 | Hakky et al. | |
| 5,236,334 A | 8/1993 | Bennett | |
| 5,242,404 A | 9/1993 | Conley et al. | |
| 5,249,583 A | 10/1993 | Mallaby | |
| 5,282,476 A | 2/1994 | Terwilliger | |
| 5,282,477 A | 2/1994 | Bauer | |
| 5,290,253 A | 3/1994 | Kira | |
| 5,324,306 A | 6/1994 | Makower et al. | |
| 5,334,183 A | 8/1994 | Wuchinich | |
| 5,335,671 A | 8/1994 | Clement | |
| 5,368,029 A | 11/1994 | Holcombe et al. | |
| 5,368,045 A | 11/1994 | Clement et al. | |
| 5,383,874 A | 1/1995 | Jackson et al. | |
| 5,397,462 A | 3/1995 | Higashijima et al. | |
| 5,400,798 A | 3/1995 | Baran | |
| 5,439,474 A | 8/1995 | Li | |
| 5,458,112 A | 10/1995 | Weaver | |
| 5,469,860 A | 11/1995 | De Santis | |
| 5,471,994 A | 12/1995 | Guirguis | |
| 5,479,486 A | 12/1995 | Saji | |
| 5,485,917 A | 1/1996 | Early | |
| 5,492,130 A | 2/1996 | Chiou | |
| 5,496,860 A | 3/1996 | Matsumoto et al. | |
| 5,511,556 A | 4/1996 | DeSantis | |
| 5,526,822 A | 6/1996 | Burbank et al. | 128/754 |
| 5,535,755 A | 7/1996 | Heske | |
| 5,546,957 A | 8/1996 | Heske | |
| 5,554,151 A | 9/1996 | Hinchliffe | |
| 5,560,373 A | 10/1996 | DeSantis | |
| 5,564,436 A | 10/1996 | Hakky et al. | |
| 5,569,284 A | 10/1996 | Young et al. | |
| 5,575,293 A | 11/1996 | Miller et al. | |
| 5,591,170 A | 1/1997 | Spievack et al. | |
| 5,601,583 A | 2/1997 | Donahue et al. | |
| 5,601,585 A | 2/1997 | Banik et al. | |
| 5,602,449 A | 2/1997 | Krause et al. | |
| 5,617,874 A | 4/1997 | Baran | |
| 5,649,547 A | 7/1997 | Ritchart et al. | |
| 5,655,542 A | 8/1997 | Weilandt | |
| 5,655,657 A | 8/1997 | Roshdy | |
| 5,665,101 A | 9/1997 | Becker et al. | |
| 5,669,394 A | 9/1997 | Bergey et al. | |
| 5,699,909 A | 12/1997 | Foster | |
| 5,700,265 A | 12/1997 | Romano | |
| 5,709,697 A | 1/1998 | Ratcliff et al. | |
| 5,720,760 A | 2/1998 | Becker et al. | |
| 5,735,264 A | 4/1998 | Siczek et al. | |
| 5,752,923 A | 5/1998 | Terwilliger | |
| 5,755,714 A * | 5/1998 | Murphy-Chutorian | 606/15 |
| 5,766,135 A | 6/1998 | Terwilliger | |
| 5,769,086 A | 6/1998 | Ritchart et al. | |
| 5,769,795 A | 6/1998 | Terwilliger | |
| 5,775,333 A | 7/1998 | Burbank et al. | |
| 5,779,649 A | 7/1998 | Herbert | |
| 5,788,651 A | 8/1998 | Weilandt | |
| 5,792,167 A | 8/1998 | Kablik et al. | |
| 5,807,282 A | 9/1998 | Fowler | |
| 5,817,033 A | 10/1998 | DeSantis et al. | |
| 5,817,034 A | 10/1998 | Milliman et al. | |
| 5,823,970 A | 10/1998 | Terwilliger | |
| 5,827,305 A | 10/1998 | Gordon | |
| 5,830,219 A | 11/1998 | Bird et al. | |
| D403,405 S | 12/1998 | Terwilliger | |
| 5,857,982 A | 1/1999 | Milliman et al. | |
| 5,879,365 A | 3/1999 | Whitfield et al. | |
| 5,908,233 A | 6/1999 | Heskett et al. | |
| 5,913,857 A | 6/1999 | Ritchart et al. | |
| 5,916,198 A | 6/1999 | Dillow | |
| 5,916,229 A | 6/1999 | Evans | 606/171 |
| 5,928,164 A | 7/1999 | Burbank et al. | |
| 5,944,673 A | 8/1999 | Gregoire et al. | |
| 5,951,490 A | 9/1999 | Fowler | |
| 5,951,575 A | 9/1999 | Bolduc et al. | |
| 5,964,716 A | 10/1999 | Gregoire et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 5,980,545 A | 11/1999 | Pacala et al. | |
| 6,007,495 A | 12/1999 | Matula | |
| 6,007,497 A | 12/1999 | Huitema | |
| 6,007,556 A | 12/1999 | Kablik et al. | |
| 6,017,316 A * | 1/2000 | Ritchart et al. | 600/567 |
| 6,018,227 A | 1/2000 | Kumar et al. | |
| 6,019,733 A | 2/2000 | Farascioni | |
| 6,022,324 A | 2/2000 | Skinner | |
| 6,022,325 A | 2/2000 | Siczek et al. | |
| 6,027,458 A | 2/2000 | Janssens | |
| 6,036,657 A | 3/2000 | Milliman et al. | |

(56) References Cited

U.S. PATENT DOCUMENTS

| | | | |
|---|---|---|---|
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,638,235 B2 | 10/2003 | Miller et al. ............... 600/566 |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,494,473 B2 | 2/2009 | Eggers et al. |
| 7,510,534 B2 | 3/2009 | Burdorff et al. |
| 7,513,877 B2 | 4/2009 | Viola |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,828,746 B2 | 11/2010 | Teague |
| 7,854,706 B2 | 12/2010 | Hibnner |
| 7,871,384 B2 | 1/2011 | Thompson et al. |
| 7,883,476 B2 | 2/2011 | Miller et al. |
| 7,883,494 B2 | 2/2011 | Martin |
| 7,974,681 B2 | 7/2011 | Wallace et al. |
| 8,016,844 B2 | 9/2011 | Privitera et al. |
| 8,073,008 B2 | 12/2011 | Mehta et al. |
| 8,190,238 B2 | 5/2012 | Moll et al. |
| 8,206,409 B2 | 6/2012 | Privitera et al. |
| 8,277,393 B2 | 10/2012 | Miller et al. |
| 8,313,444 B2 | 11/2012 | Thompson et al. |
| 8,343,069 B2 | 1/2013 | Uchiyama et al. |
| 8,597,205 B2 | 12/2013 | Seiger et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0065474 A1 | 5/2002 | Viola ........................ 600/564 |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |

(56) References Cited

U.S. PATENT DOCUMENTS

| | | |
|---|---|---|
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1* | 1/2004 | Angel ........................... 600/564 |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0080355 A1 | 4/2005 | Mark |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1* | 5/2005 | Schwindt et al. .............. 600/566 |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0165329 A1 | 7/2005 | Taylor et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1 | 7/2009 | Hibner et al. |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0152715 A1 | 6/2011 | Delap et al. |
| 2011/0160611 A1 | 6/2011 | Ritchart et al. |
| 2011/0208085 A1 | 8/2011 | McCullough et al. |
| 2011/0295150 A1 | 12/2011 | McCullough et al. |
| 2011/0313316 A1 | 12/2011 | Ranpura et al. |
| 2012/0065541 A1 | 3/2012 | Videbaek |
| 2012/0071787 A1 | 3/2012 | Reuber et al. |
| 2012/0095366 A1 | 4/2012 | Heske et al. |

(56) References Cited

U.S. PATENT DOCUMENTS

| | | |
|---|---|---|
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0190648 A1 | 7/2013 | Videbaek |
| 2013/0197391 A1 | 8/2013 | Videbaek |
| 2013/0204161 A1 | 8/2013 | Videbaek et al. |
| 2013/0289441 A1 | 10/2013 | Videbaek et al. |

FOREIGN PATENT DOCUMENTS

| | | |
|---|---|---|
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9624289 A2 | 8/1996 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |

* cited by examiner

TRANSPORT SYSTEM FOR BIOPSY DEVICE

CROSS-REFERENCE TO RELATED APPLICATIONS

This application is a U.S. national phase of International Application No. PCT/DK2005/000484, filed Jul. 8, 2005, which claims the benefit of U.S. Provisional Application No. 60/586,290, filed Jul. 9, 2004, U.S. Provisional Patent Application No. 60/625,127, filed Nov. 5, 2004, and U.S. Provisional Patent Application No. 60/625,128, filed Nov. 5, 2004.

TECHNICAL FIELD

The present invention relates to a biopsy device for harvesting tissue samples of human or animal bodies. The invention is particularly, but not exclusively, aimed at percutaneous biopsy, in which it is desirable to gain access to suspect tissue mass in a minimally invasive manner. The invention is particularly concerned with aspects of conveying a sample-receiving device containing one or more harvested tissue sample in an outer hollow needle of the biopsy device.

BACKGROUND OF THE INVENTION

For diagnostic purposes it may be desirable to obtain a tissue sample of a human or animal body for in vitro cytological and/or histological examination. Tissue sampling may be performed either as an open or a percutaneous technique. In the open technique, either the entire suspect mass (excisional biopsy) or part of the suspect mass (incisional biopsy) is removed. Access to the lesion as well as removal is generally obtained with the use of scalpels, and open biopsies are a reliable—if quite invasive—means of obtaining tissue samples.

In the percutaneous technique, a needle is used to gain access to the suspect tissue mass in a less invasive fashion. This needle may be hollow, permitting the aspiration of single cells and tissue fragments into a lumen by application of a vacuum (aspiration biopsy). Alternatively, larger tissue cores may be harvested by means of a needle containing an inner movable trocar with a notch formed to receive tissue cores, and an outer, slidable cannula with a sharpened distal end used to sever these cores from the surrounding tissue (core needle biopsy). By advancing the inner trocar into a suspect lesion and subsequently advance the outer slidable cannula to cover the notch completely, a tissue sample may be severed and held in the notch. The needle may then be retracted from the body of the patient, and the tissue sample may be collected and stored for further analysis.

Core needle biopsy devices have been preferred tools among physicians due to their simple use and versatility. The core needle devices may be applied to a broad range of different tissues and different anatomical locations, and provide the pathologist with samples suitable for histological analysis for the accurate diagnosing and staging of suspect masses.

Obtaining the largest possible sample size is an important objective in the harvesting of core tissue samples. Prior art biopsy systems have used vacuum to engage and draw tissue towards the notch or tissue-receiving chamber or basket of the biopsy device prior to cutting. Thus, tissue sample sizes may be significantly increased with a given biopsy needle diameter or larger samples extracted with the same needle diameter to improve diagnostic accuracy.

Another well-known prior art technique to increase sample size is to harvest multiple samples in order to obtain sufficient tissue for a reliable diagnosis. To do so with the aspiration, core needle biopsy devices or single-action vacuum-assisted devices is only possible through multiple device insertions, resulting in increased patient discomfort, time consumption and risk of bleeding.

In the area of breast biopsies, this problem has been solved with the development of biopsy systems enabling the operator to extract multiple samples with a single biopsy device insertion. These biopsy devices generally apply vacuum to engage and aspirate a suitable amount of tissue into a hollow portion of the instrument. The power and vacuum supply units pertaining to those multiple biopsy devices are housed in separate vacuum stations that require carts for transportation as well as hoses and leads to function properly. The physical connection between the biopsy device and the accompanying vacuum/power supply units means that the freedom of movement of the operator or physician is limited, and auxiliary devices furthermore take up storage and floor space.

In prior art biopsy systems and devices tissue sample extraction, ejection and subsequent storage of the individual tissue samples have been accomplished by a number of different methods. Some biopsy devices comprise mechanical extraction and ejection of extracted tissue samples, as illustrated in U.S. Pat. No. 5,526,822. The biopsy device captures and holds the tissue sample in a lumen of an inner, rotating cutting cannula that is retractable to a point outside the anatomy of the patient. An ejector pin is utilized to push the captured tissue sample out of the lumen of the cannula.

Other prior art biopsy devices feature vacuum-driven extraction and ejection of tissue samples. U.S. Pat. No. 6,638, 235 discloses a biopsy device with an inner, rotating cutting cannula capable of harvesting multiple tissue samples in a single cannula insertion. The device reduces operator involvement by enabling the automatic extraction and collection of multiple tissue samples in a collection chamber placed outside the anatomy of the patient. Tissue samples are extracted from the point of sampling and moved through the inner lumen of the cutting cannula to the collection chamber by means of a vacuum that is drawn through the collection chamber and the inner lumen of the cutting cannula.

In the sampling, collection and storing of some types of tissue samples, such as prostate tissue samples, it is desirable that extracted individual tissue cores or samples are kept apart if a subsequent diagnosis is to be valid.

SUMMARY OF THE INVENTION

It is an object of preferred embodiments of the present invention to provide a biopsy device and a method that may permit sampling, preferably in an automatic manner. It is a further object of preferred embodiments of the invention to provide a biopsy device and a method, which allow for convenient penetration of suspect tissue mass. It is a still further object of preferred embodiments of the invention to provide a biopsy device and a method, which allow for convenient severing of a tissue sample. It is a still further object of preferred embodiments of the invention to provide a biopsy device and a method, which facilitate handling of acquired tissue samples by a physician. It is a still further object of preferred embodiments of the invention to provide a biopsy device, which is conveniently maneuverable by a physician. It is a still further object of preferred embodiments of the invention to provide a biopsy device and a method, which allow for storing of individually separated tissue samples in a preserving agent.

In a first aspect, the invention provides a biopsy device for harvesting at least one tissue sample from a body of a living being, the device comprising:

a hollow needle with a distal end portion adapted to be introduced into the body;

a cutting mechanism for severing the at least one tissue sample;

a sample-receiving device with a cavity for receiving the at least one severed tissue sample, the sample-receiving device being receivable in the hollow needle and movable therein;

a transport device for moving the sample-receiving device in the hollow needle, the transport device comprising a bendable elongate element.

The transport device (or transport mechanism) may be coupled with the cutting mechanism and a compact driver system featuring all necessary controls and mechanics. An optional vacuum supply unit for aspirating (or sucking) tissue into the cavity of the sample-receiving may either be integrated with a handle unit or it may be arranged in an external or freestanding unit. The transport mechanism preferably enables the collection and removal of multiple tissue samples in a fast, efficient and reliable procedure. The cutting mechanism preferably enables the instant and efficient severing of tissue samples. This may e.g. be accomplished with rotating cutters of spring-loaded mechanisms, although electro-cautery is also applicable. The handle unit may comprise drivers that deliver the necessary actuation forces and motions to the transport and cutting mechanisms. This may e.g. be accomplished through several means, the most common being springs, electric motors or air-powered drives.

The transport device of the present biopsy device may include any suitable system for moving the sample-receiving device in the hollow needle, i.e. any system capable of pulling the sample-receiving device from a first extended (i.e. distal) position to a second retracted (i.e. proximal) position and of pushing the sample-receiving device from the second retracted position to the first extended position. The transport device for moving the sample-receiving device in the hollow needle comprises a bendable elongate element, such as a steel wire, two or more twisted wires, such as a Bowden cable or any other flexible or bendable element. The elongate element is preferably bendable away from the longitudinal direction of the hollow needle, i.e. laterally bendable, and it preferably has sufficient stiffness or sufficient support in lateral directions to prevent the bendable elongate element from flexing outwardly when the sample-receiving device is to be pushed from the second retracted position to the first extended position.

Preferably, a coiling device is provided for coiling up the bendable elongate element, the coiling device being preferably arranged at a proximal end of the device, such as at least proximal of the second retracted position. In embodiments, in which the bendable elongate element is comprised in a disposable unit, which is attachable to e.g. a handle-unit or a stationary unit of the biopsy device, the coiling device is preferably integrated in the disposable unit as elaborated in more detail below.

The bendable elongate element may have a longitudinally extending portion of circular or non-circular cross section, such as e.g. polygonal cross-section, such as triangular or rectangular. A polygonal cross-section confers the possibility that the bendable elongate element may be toothed for engagement by a driving gearwheel. Thus, in one embodiment, the bendable elongate element comprises a row of regularly spaced teeth extending substantially perpendicularly to a longitudinal axis of the elongate element. In this embodiment, the biopsy device may have a rotatable gear wheel having a rim with teeth for interacting with the teeth of the elongate element so as to move the elongate element in the hollow needle along the longitudinal axis. One or more supports may be provided for supporting the bendable elongate element in the lateral direction to avoid flexing thereof, the support(s) comprising e.g. two opposing wall sections arranged with a mutual clearance corresponding to a thickness of the bendable elongate element, the bendable elongate element being free to slide in the longitudinal direction between the wall sections. Similarly, the bendable elongate element may slide between opposing roller elements.

In order to allow the sample-receiving device to rotate relative to the bendable elongate element, the sample-receiving device may be secured or attached to the bendable elongate element by means of a swivel joint.

From the above discussion, it will be appreciated that the sample receiving device may have a length, which is substantially shorter than a length of the hollow needle, and that a distal end of the bendable elongate element may be attached to a proximal end of the sample-receiving device, so that the bendable elongate element causes movement of the sample-receiving device in the hollow needle.

It will also be understood that the biopsy device of the present invention may comprise a handle unit with a power source and a motor for driving the transport device, and that the transport device, the hollow needle and the sample-receiving device may be comprised in a disposable unit, which is releasably secured to the handle unit. A driving interface is preferably provided to transmit a driving force from the motor in the handle unit to the bendable elongate element in the disposable unit.

The coiling device is likely to be contaminated by body tissue and/or body fluids during tissue sample harvesting, as the bendable elongate moves in the hollow needle, the inner wall of which may be in contact with the tissue sample, when the tissue sample is being moved in the cavity of the sample-receiving device. Thus, the coiling device is preferably comprised in the disposable unit. Irrespective of whether the coiling device is comprised in the disposable unit or in other parts of the biopsy device, such as in the handle unit, the coiling device may form a spiral. The spiral may e.g. be formed by at least one wall element, which is arranged such that contact between coiled-up portions of the bendable elongate element is prevented to avoid uncontrolled bending or varying dimensions of a coiled bendable elongate element.

Embodiments of the biopsy device of the present invention, which form a handheld unit, preferably also include the transport device, e.g. the bendable elongate element, in the handheld unit. It will be appreciated that the handle unit preferably is embodied as a hand held unit, which accommodates all required power, liquid and vacuum sources as well as possible driving mechanisms for needle and sample-receiving device and firing mechanisms, cf. below. Generally, the entire biopsy device of the present invention, including the hollow needle, the cutting mechanism, the sample-receiving device, the transport device, an optional liquid supply unit and all other structural elements mentioned herein may be comprised in a hand-held unit.

Further embodiments and features will become apparent from the below description.

Transfer of samples from the point or position of sampling (or harvesting site) to the point or position of collection (or sample ejection) is preferably carried out by means of a flat, toothed bar, preferably of a polymer material such as polypropylene, to which the sample-receiving device is attached, the sample-receiving device being e.g. in the form of a canoe-like container to hold tissue samples once they have been severed. The sample-receiving device may have a side-facing opening for receiving tissue samples, and may have one or several vacuum ports to enable the aspiration of tissue into the sample-receiving device by application of vacuum. Severing of tissue samples may be carried out by means of a coaxial, piston-like system comprising a spring-loaded outer cutting cannula (i.e. the hollow needle) with a sharpened distal end (i.e. the circumferential cutting edge) and capable of axial movement, and a an inner guiding cannula with a sharpened tip capable of penetrating tissue as the biopsy device is positioned in the tissue to be sampled. The inner guiding cannula may be non-movable or movable by the transport device described herein. The inner cannula may have a side-facing notch (or cavity) enabling tissue to prolapse into the inner lumen of the cannula and into the waiting sample-receiving device. The transport system for the sample-receiving device and/or for the severed tissue sample is axially movable within the inner lumen of the inner cannula, e.g. to advance and retract the sample-receiving device. Power for driving the transport mechanism may be delivered by an electric or pneumatic driver unit. Expelling of samples from the sample-receiving device and into a suitable transport container may be done by means of liquid or pressurized air at the point of collection (or ejection).

The bendable elongate element may comprise a flat bar, toothed on one side, and it may be made from a suitable polymer material such as polypropylene or Nylon™. The bendable elongate element is moved longitudinally in the cannula system and enables the transport of tissue samples from the harvesting site at the distal tip of the biopsy device, e.g. the first extended position of the sample-receiving device, to the point of ejection, e.g. the second retracted position of the sample-receiving device. It may fit tightly to the wall of the inner cannula to ensure lateral stiffness once it enters the cannula. A cavity on the upper side may enable the application of vacuum to the distal end of the system. The distal point of the cannula system may feature an attachment device to enable the temporary coupling of the cannula with the suspect tissue mass, e.g. a tumour.

The bendable elongate element (or bar) may be coupled with a sample-receiving device with a vacuum gate. This vacuum gate may have several different configurations, depending on the application and the design of the expelling (i.e. flushing) chamber. The flat toothed bar may establish a vacuum channel in the cannula. The sample-receiving device may receive the tissue during the sampling procedure and hold the sampled tissue on its way from the point of sampling or harvesting to the point of collection. A filter or grid may be provided to ensure that no tissue escapes the container.

A coupling mechanism between the toothed bar and the sample-receiving device may permit a swiveling motion of the sample-receiving device relative to the flat bar as the sample-receiving device is readied for emptying (or ejection), to facilitate the emptying procedure.

The toothed bar may interact with a pinion, allowing the conversion of rotational motion of the pinion to linear motion of the toothed bar to enable the withdrawal of harvested tissue samples and the positioning of the sample-receiving device in the cannula system, i.e. in the outer hollow needle. The pinion may be of metal or a ceramic material to ensure longevity.

The motor for driving the sample receiving device or pinion may be an electric motor. Two batteries and a switch (on/off switch) may be provided for activating and driving the motor. The motor may be pneumatic, which may render the system MRI-compatible.

The coiling device may comprise a spool-like component placed in the handle to enable the coiling-up of the toothed bar as it is retracted. Hereby the toothed bar will not protrude far beyond the proximal end of the transport mechanism. This is an advantage, in particular when taking biopsies at deep anatomical depths. Alternatively, the toothed bar can be bent away form its longitudinal direction.

A guiding wheel may be incorporated to stabilize the flat bar and the sample-receiving device as the assembly is advanced into the cannula system.

A driver unit of the biopsy device may comprise the following components: One or more motors integrated in a suitably designed handle. The motor may generally have two main functions, namely to advance and retract the flat, toothed bar with the sample-receiving device, and to cock and release the firing mechanism when a sample has been readied for cutting. The cocking of the cutting mechanism may result automatically once the system is put into operation, with the retraction, emptying and extension of the sample-receiving device automatically following the firing of the cutting mechanism. Control of the device may result e.g. from the depressing of a pedal or a selection of buttons. The driver unit may be either electrically or pneumatically driven, and it is preferably an independent, completely freestanding unit with its own power supply, vacuum-source and tissue collection container. It may be configured to enable (by selection) one or more of the following operation modes: stepwise, semi-automatic or fully automatic.

The vacuum supply and the expelling mechanism may either be integrated parts of a handle housing the driver unit, or they may be placed in an external unit. The expelling mechanism (or ejection system) may utilize air pressure, water flushing or a third means of expelling the tissue.

As an alternative to the toothed bar, a wire, e.g. a steel wire, may be used as a transport mechanism. The steel wire can be a single wire, or it can have two or more twisted wires, with or without a core wire, a principle known from the so-called Bowden cables. The Bowden cable may be coiled up as described above. To enable the functioning of such a wire, the spool used to coil up the wire may have a groove in its surface tailored to the dimensions of the wire, and the spool may be suspended in a tight-fitting housing unit, whereby a channel is formed for the wire. The use of a stiff wire, in combination with the tailored channel, enables the retraction and advancement of the sample-receiving device within the guiding cannula.

In a default position of the biopsy device, the flat bar with the sample-receiving device may be maximally extended, and the sample-receiving device may be placed in the distal end of the cutting system. The outer cannula may be maximally extended, covering the tissue-receiving port in the inner cannula as the system is advanced into the body of the patient.

When a sampling sequence is initiated, the driver unit may be activated to start cocking of a spring-loaded firing mechanism as described in more detail below, and the outer cannula may be pulled towards the proximal end of the device, opening the tissue-receiving port. Once the outer cannula has been retracted to open the tissue receiving port, a vacuum may be applied to the inner lumen of the inner cannula, sucking tissue into the tissue receiving port and into the sample-receiving device.

After the cutting mechanism has been retracted, the sample taking mechanism may release the spring-loaded firing mechanism, rapidly advancing the outer cannula to sever the tissue sample. Upon severing of the tissue sample, the flat, toothed bar with the sample-receiving device may be retracted and carry the biopsy sample towards the point of collection (or ejection).

A mechanism at the proximal end of the inner cannula may engage and swivel the sample-receiving device when it exits the inner cannula to facilitate the expelling (or ejection) of samples. As the sample-receiving device enters the expelling chamber, a stream of liquid may automatically be released to flush the tissue sample out of the sample-receiving device and into a suitable container. The flushing liquid is preferably saline, possibly containing additives for preserving the sample or preparing it for examination.

Having completed the expelling cycle, the flat, toothed bar and the sample-receiving device are advanced, and the sample-receiving device may be positioned in the distal end of the inner cannula in preparation of a new cycle. On the completion of the sampling sequence, the outer cannula may be left in the default position to close the tissue receiving port in preparation of the removal of the biopsy needle. The tissue storage container may be detached from the biopsy device and sent to the pathologist for further analysis.

A tip of the sample-receiving device may be conical, and it may be configured to serve as a penetration point, tissue-receiving port, sample container and a cutting board.

In the present invention, the outer diameters of biopsy needles may be within the range from 0.5 mm to 5.0 mm, such as in the range from 1.2 mm to 3.0 mm. Biopsy needles are typically made of stainless steel, but other materials can be used such as titanium, which is MRI compatible.

In order to accurately control movement of the sample-receiving device in the hollow needle, the sample-receiving device and the hollow needle may be shaped, so that relative rotational displacement between the sample-receiving device and the hollow needle in said plane is prevented. For example, the outer cutting cannula or hollow needle may comprise first orientation means adapted to co-operate with mating second orientation means of the sample-receiving device, so as to guide and orient the sample-receiving device in a plane substantially perpendicular to the axis of movement of the sample-receiving device inside the outer cutting cannula. The orientation means may ensure reliable positioning of a sample ejection aperture of the sample-receiving device in a plane substantially perpendicular to the axis of movement thereof, so as to support automated ejection of extracted tissue samples. For example, the oval cutting cannula and the sample-receiving device may have oval profiles, or an inward protuberance may be provided on an inner wall of the cutting cannula (outer needle), the protuberance engaging a corresponding groove in the sample-receiving device.

The biopsy device of the present invention may comprise a liquid supply unit adapted to comprise a flushing liquid, the liquid supply unit being operatively connected to the cavity of the sample-receiving device through a hollow liquid transport member so as to allow tissue sample ejection by liquid flushing.

The liquid supply unit as outlined above allows for cautious handling of the at least one harvested tissue sample during the biopsy procedure and subsequent retrieval of acquired tissue samples to maintain the structural integrity of suspect tissue and allow an accurate diagnosis to be made. Furthermore, individually extracted tissue cores or samples may advantageously be kept apart to enable better diagnostic capabilities. This is beneficial in respect of most kinds of tissue samples, such as prostate samples. In addition, liquid flushing to eject the at least one tissue sample from the cavity of the sample-receiving device allows for automated and rapid biopsy procedures with minimal patient trauma and minimal manual handling of the harvested tissue sample(s) by physicians.

The flushing liquid is preferably a preserving agent, in which the harvested tissue sample is to be stored following ejection from the cavity of the sample-receiving device. The flushing liquid may e.g. comprise saline or formalin. It will be appreciated that no rough handling of the body tissue sample, e.g. by forceps, is required in order to remove the harvested tissue sample from the cavity of the sample-receiving device, as ejection may be caused solely under the action of the flushing liquid. The cavity may have a substantially circular cross-section. Particularly advantageous embodiments of the biopsy device of the present invention are completely handheld and include integral vacuum supply and liquid supply mechanisms as well as power source, thereby eliminating any need for separate (or external) vacuum, fluid and power sources. Alternatively, the vacuum supply and/or power source could be arranged externally to the biopsy device and connected thereto by suitable electrical power conductors and vacuum hoses.

In one embodiment, the biopsy device of the present invention comprises a closed system for tissue-sample extraction and transportation to avoid leakage of bodily fluids, operator exposure to biohazards and contamination of extracted tissue samples. This embodiment ensures that manual handling of extracted tissue samples is minimized, and possible handling damage is consequently minimized.

The hollow needle preferably defines a longitudinally extending annular body portion, which defines a co-extending longitudinal cavity in the hollow needle, and the cavity in the sample-receiving device may have a lateral opening for receiving the at least one tissue sample.

In one embodiment of the present invention, the cutting mechanism comprises a circumferential cutting edge at the distal end of the hollow needle as described in more detail below. In order to allow efficient tissue severing by the circumferential cutting edge, the sample-receiving device and the hollow needle are preferably movable relative to each other, such that the sample-receiving device may be in a projecting position, in which it projects from a distal tip of the needle, and a retracted position, in which it is accommodated in the hollow needle, and in which the distal end of the device is defined by said circumferential cutting edge and possibly a tapered tip of the sample-receiving device.

In order to aspirate or suck body tissue into the cavity of the sample-receiving device, the biopsy device of the present invention preferably comprises a vacuum pump for generating a suction effect in the cavity of the sample-receiving device, the vacuum pump being in fluid communication with the cavity of the sample-receiving device through a longitudinally extending passage in the sample-receiving device and/or through the longitudinally extending passage defined by the hollow needle. For example, there may be provided one or more vacuum ports at the bottom of the sample-receiving device, such as in a wall section defining a bottom of the cavity in the sample-receiving device, through which vacuum port(s) the cavity is in fluid communication with the interior of the hollow needle, which in turn is in fluid communication with the vacuum pump. Alternatively, there may be provided one or more vacuum ports in a side wall forming a side portion of the cavity in the sample-receiving device, through which vacuum port(s) the cavity may be in fluid communication with the interior of the hollow needle or with a longitudinally extending passage in the sample-receiving device, the interior of the hollow needle or the passage in the sample-receiving device being in fluid communication with the vacuum pump. Preferably, the vacuum pump is only operated in a short period of time each time a tissue sample is to be harvested, i.e. immediately prior to severing of the tissue sample. Control of the operation of the vacuum pump may e.g. be coupled to control of the cutting mechanism and/or to control of the transport device, so that the vacuum pump is only activated when the sample-receiving device is in its first extended position or within a predefined period of time after the sample-receiving device has arrived at the first extended position, or within a predefined period of time before the cutting mechanism is activated to sever the tissue sample. Alternatively, control of the vacuum pump may be coupled to control of the cutting mechanism, e.g. such that the vacuum pump is activated when the hollow needle is retracted to lay bare the cavity of the sample-receiving device, cf. the below description of the firing mechanism for severing the tissue sample, and such that operation of the vacuum pump is deactivated when the tissue sample has been severed.

The at least one tissue sample harvested by the biopsy device of the present invention is preferably harvested in an automatic manner, extracted from the anatomy of the patient, ejected from the sampling-receiving device and individually placed in a suitable tissue storage container in a storing and/or preserving agent. Thus, the operator (or pathologist) is free to concentrate on optimizing tissue sampling and minimizing patient trauma.

In the biopsy device of the present invention, the liquid supply unit may be operatively connected to the cavity of the sample-receiving device when the sample-receiving device is in its second retracted position, and the liquid supply unit is preferably disconnected from the cavity of the sample-receiving device when the sample-receiving device is in its first extended position. The first extended position is normally the position, in which tissue is collected into the cavity of the sample-receiving device as the cutting mechanism severs the tissue sample, i.e. in the first extended position, in which the sample-receiving device with its cavity are in a distal position. The second retracted position is a proximal position, in which the harvested tissue sample may be ejected from the cavity of the sample-receiving device.

Preferably, a pump for pumping the liquid from the liquid supply unit to the cavity of the sample-receiving device is integral in the biopsy device. The pump may advantageously comprise a peristaltic pump, which is relative inexpensive. For example, the peristaltic pump may be incorporated in a handle portion of the device. In one embodiment, the peristaltic pump is releasably attached to a handle portion of the biopsy device, so that exchange of the liquid supply unit is facilitated, as the peristaltic pump engages a portion of the hollow liquid transport member (e.g. a plastic or elastomeric hose or tube). In one embodiment, a clamping mechanism is provided, which firmly holds the hollow liquid transport member in abutment with the peristaltic pump, the clamping mechanism preferably being releasable by hand. As an alternative, or in addition to the peristaltic pump, the liquid supply unit may comprise a syringe-like liquid supply chamber and a plunger movably disposed in the liquid supply chamber. Like the pump, the liquid supply unit may be releasably secured to the handle unit, so as to allow for convenient exchange thereof.

The biopsy device of the present invention may comprise a handle unit, which houses or incorporates a power source, such as a battery pack, and a motor for driving the transport device. The handle unit preferably incorporates no means or elements, which come into physical contact with body tissue, body fluid or the patient's anatomy during tissue harvesting, so that the handle unit may be re-usable, i.e. usable for several biopsy procedures that each may involve extraction of multiple tissue samples from a patient. The transport device, the hollow needle and the sample-receiving device, which are parts which are likely or inevitably come into contact with body tissue, body fluid or the patient's anatomy during tissue harvesting, are preferably comprised in a disposable unit, which is releasably secured to the handle unit. The disposable unit is intended to be used for one single biopsy procedure and to be disposed of following harvesting of one or more tissue sample from a harvesting site in the patient anatomy. As described in detail below, multiple tissue samples may be harvested by means of preferred embodiments of the biopsy device without exchanging the disposable unit, once the outer hollow needle of the disposable unit is in place at the harvesting site.

A flushing chamber may be provided, preferably in the disposable unit, the flushing chamber being adapted for attachment of a sample-collecting container to the biopsy device. Hence, the sample-receiving device is preferably aligned with the flushing chamber in the second retracted position, however other layouts are contemplated, in which the harvested tissue sample is conveyed by means of the flushing liquid from the cavity in the sample-receiving device to flushing chamber and from there to the sample-collecting container. The sample-collecting container may define at least one cavity, and preferably a plurality of cavities for receiving the harvested tissue sample, whereby one or more cavities may communicate with the cavity of the sample-receiving device, when the sample-receiving device is in its second retracted position. The sample-collecting container is preferably releasably mounted to the disposable unit. The at least one cavity for receiving the tissue sample may e.g. comprise a plurality of cavities for receiving individual tissue samples, the sample-collecting container further comprising a movement or rotation mechanism for changing the relative position of the cavities relative to the sample-receiving device, so that different tissue samples harvested at different times can be flushed into separate cavities. For example, the cavities may be circularly disposed on a rotatable disk, rotation of which is controlled by a control system of the biopsy device (or biopsy system) to automatically align a subsequent container cavity with the flushing chamber and/or sample-receiving device, when a body tissue sample has been ejected into a previous container cavity.

The sample-collecting container, also referred to as the "tissue storage container", may e.g. have a volume of 10-100 ml, such as 20-30 ml. The liquid supply unit or liquid container may e.g. have a volume of 5-30 ml, such as 5-15 ml, such as approximately 10 ml.

The flushing chamber may be connected to an outlet valve of the fluid supply unit, which may be pressurized as described. An opening in a wall of the flushing chamber permits liquid to move from the pressurised liquid supply unit into the flushing chamber. On a side of the flushing chamber, opposite the pressurised liquid supply opening, a drain may be provided leading to the tissue storage container, where extracted tissue samples may be individually stored. This drain may be opened and closed by a sliding valve or another suitable closure mechanism.

The flushing liquid impacts and dislodges a tissue sample held in the cavity of the sample-receiving device, the tissue sample being ejected through the cavity of the sample-receiving device. The flushing liquid subsequently carries the tissue sample through the drain and into the tissue storage container. The flow of flushing liquid into and out of the flushing chamber is controllable by operation of the slidable valve. In one embodiment, the slidable valve is operatively connected to a valve spring which ensures that the valve in its default position closes the opening leading to the pressurised fluid supply as well as the drain leading to the tissue storage container. Alternatively, opening and closing of the valve may be caused by the transport device for moving the sample-receiving device in the hollow needle, the transport device comprising e.g. a bendable elongate element. Thus, a portion of the transport device may interact with the valve or with a means for opening and closing the valve. In general, means may be provided, which prevent that flushing liquid is being drawn into the inner lumen of the hollow needle when vacuum is applied to suck tissue into the cavity of the sample-receiving device.

When the sample-receiving device is moved towards the second retracted position, the sample-receiving device or the transport device is brought in contact with the slidable valve. The continued retraction of the sample-receiving device causes the slidable valve to be pushed towards the back of the flushing chamber so that the opening leading to the liquid supply unit and the drain leading to the tissue storage container are both opened. This operation permits fluid to enter the flushing chamber, and the sample to move through the drain into the storage container. During this process, the vale spring is energized with potential energy by mechanical compression or with electrical energy. After a tissue sample has been flushed out of the sample-receiving device, it is once again advanced towards the first extended position, whereby the valve is closed, e.g. by electrical energy or by release of potential energy stored in the spring.

The tissue storage container may be substantially circular and comprise a number of separate identifiable chambers, wherein each chamber is adapted to receive a tissue sample. The storage container may comprise a movable part operatively connected to a suitable driver mechanism in a driver unit, e.g. the handle unit, so as to permit the automatic change of chambers as the biopsy procedure progresses and multiple tissue samples are harvested. Thus, a single tissue sample is preferably captured in each chamber, and the subsequent change of chambers ensures that each tissue sample and its associated storage liquid are confined in the tissue storage container.

Individual tissue samples may subsequently be identified through their respective placement in the sample-receiving device, and individual chambers may furthermore be named, coded or otherwise made recognisable/identifiable. A counter may be included to assist the operator in keeping track of the number of biopsies taken. In order to further automate the biopsy procedure several of all of the chambers of the tissue storage container may be partially pre-filled with a preserving agent such as concentrated formalin or another suitable preserving agent. In this way, the flushing liquid injected into the flushing chamber serves at least two purposes, (1) to carry the tissue sample from the sample-receiving device into the storage container, and (2) to adjust the concentration of the preserving agent in the storage container to a level suitable for the preservation of tissue samples.

In order to facilitate tissue penetration of the sample-receiving device, the sample receiving device may comprise or be formed as a cannula with a sharpened distal tip. The cannula extends coaxially with the hollow needle in the hollow needle.

One alternative embodiment of the vacuum-flush mechanism previously described employs twin syringe-plunger systems as an alternative to a syringe-plunger system and a vacuum-working fan. The present vacuum-flush mechanism comprises of twin syringe chambers, each with a plunger slidably disposed in the inner cavity of each chamber.

A first chamber functions as a vacuum supply unit and comprises two openings, each fitted with a one-way valve. One valve permits air to enter an inner cavity of the chamber when the plunger pertaining to this chamber is retracted. This valve is in fluid communication with the proximal end of the cutting cannula. When the plunger is retracted, air is drawn out of the inner lumen of the hollow needle and a vacuum is created. This vacuum is communicated through the inner lumen of the hollow needle and into the inner cavity or tissue cavity of the sample-receiving device where it engages and aspirates tissue through the lateral opening of the sample-receiving device and into the inner cavity of the container. Another valve permits air to escape when the plunger is moved forward.

The vacuum supply plunger may be powered by a rack-and-pinion system or another coupling mechanism housed in the handle unit.

Another unit comprises a pressurised liquid supply unit. It comprises of a syringe-like chamber and a plunger movably disposed inside said chamber, and has two openings, each fitted with a one-way valve. One valve permits the flushing fluid such as saline, water etc. to enter the cavity defined by the chamber when the plunger pertaining to this chamber is retracted. This valve is connected to a liquid supply with a tight connection. The liquid supply may comprise a plastic container with relatively soft walls, so that in response to retraction of the plunger, flushing liquid is drawn from the liquid supply unit and into the inner cavity of the chamber. The walls of the plastic container collapse inward as the container empties, ensuring that no air gets into the system. By subsequent forward movement of the plunger, the flushing liquid is ejected from the inner cavity of the chamber and through the outlet valve into a flush-out chamber.

The pressurised liquid supply plunger is operatively connected to the driver unit and backward motion may be provided by a suitable power-transmitting component or coupling means mounted for example on the shaft of the plunger. The forward motion of the plunger is preferably powered by a spring that is operatively connected to the shaft of the plunger. When the shaft of the plunger is moved backwards, potential energy is stored in the spring. At a given point, the shaft is released, and the potential energy stored in the spring is released to move the plunger forward and eject the flushing liquid from the chamber. At the end of the biopsy cycle, the plunger shaft is once again engaged by the power-transmitting mechanism, and a new cycle may be initiated.

The biopsy device of the present invention may further comprise:

a first user-operable firing mechanism for causing the hollow needle and the sample-receiving device to be longitudinally displaced in a distal direction, so as to penetrate body tissue at or near the suspect tissue mass;

a second user-operable firing mechanism for causing the hollow needle to be longitudinally displaced in a distal direction from a first position, in which the sample-receiving device projects from the distal end of the hollow needle, to a second position, in which the hollow needle essentially accommodates the cavity of the sample-receiving device, so as to sever said tissue sample from remaining body tissue at the harvesting site.

It should be understood that the first user-operable firing mechanism is optional, i.e. the biopsy device may include only the second firing mechanism. The first firing mechanism may advantageously be incorporated in a separate module, which may or may not be mounted to the device during assembling thereof.

The first firing mechanism is useful for penetrating a suspect tissue mass, e.g. a tumour, penetration of which may be difficult due to e.g. hardness or due to a loosely supported attachment of the suspect tissue mass to surrounding tissue of the body. The loosely supported attachment may cause the suspect tissue mass to displace by pressure from the tip of the biopsy needle and to slide past the suspect tissue mass without penetrating it. It has been found that, by firing the inner and outer needles substantially simultaneously, preferably at a relatively high speed, it is possible to contact and penetrate even a loosely supported tissue mass. Below, the substantially simultaneous firing of the outer needle and the sample-receiving device will be referred to as a "double shot".

The biopsy device may comprise a control system for the first and second user-operable firing mechanisms, the control system being configured such that only one of the firing mechanisms can be activated at a time. The control system may be based on electronic control means, which provide a control signal to one or more motor(s) and other elements of the firing mechanisms. In order to expedite tissue harvesting, the control system may be configured to automatically activate the second firing mechanism after firing of the first firing mechanism, i.e. so that a tissue sample is automatically severed upon penetration of the suspect tissue mass.

The first and second firing mechanism may comprise respective energy storage and release mechanisms. The energy to be stored may e.g. be provided by an electrically driven motor. The energy release mechanisms may be controlled to substantially instantaneously release the stored energy to fire the outer hollow needle and the sample-receiving device substantially simultaneously (double shot, first firing mechanism) or to fire the outer hollow needle solely ("single shot", second firing mechanism). The energy storage means may e.g. comprise springs, such as compression springs. Thus, the first firing mechanism may comprise a first compression spring, and the second firing mechanism may comprises a second compression spring, and the device may further comprise at least one loading mechanism for loading the first and second springs and for releasing the springs upon loading thereof. The loading mechanism may comprise one or more elements for transmitting a displacement of one or more actuators to the springs. The actuator(s) may e.g. comprise at least one linear actuator and/or at least motor, the rotational motion of which may be converted into linear displacement of one or both compression springs. Such conversion of motion may e.g. be provided via a gear/rack drive, or via abutment of a member protruding from a surface of a rotational wheel with a linearly displaceable member. For most applications, the force provided by each of the first and second springs may be 20-150 N, such as 40-80 N, such as approximately 50 N.

The first firing mechanism may be connected to a needle driving member, which is secured to the hollow needle to transmit the firing force of the first spring or other energy storage means to the hollow needle. The first and second firing mechanisms, the hollow needle, the sample-receiving device and the needle driving member are preferably comprised in a disposable unit, which is releasably attached to the handle unit. The first spring is preferably connectable to the transport device for moving the sample-receiving device in the hollow needle, and the first spring may further be connected to the needle-driving element. Thereby, the hollow needle and the sample-receiving device may be longitudinally displaced upon release of the first firing mechanism.

A first power-driven element, e.g. a motor, may be provided for driving the transport device to move the sample-receiving unit backward and forward in the hollow needle. In order to minimize resistance to the firing force provided by the first firing mechanism, the loading mechanism may be configured to, upon loading of the first spring, decouple the transport device from the motor, the transport device being preferably movable along with the sample-receiving device in the hollow needle at firing of the first firing mechanism. In one embodiment, motion of the motor is transmitted to the transport device, comprising e.g. a bendable elongate element, via a gear drive. That gearwheel of the gear drive, which engages the transport device, may be left in engagement with the transport device for stabilization thereof during firing of the first firing mechanism. Thus, decoupling of the transport device from the motor may be performed at a location, which is closer to the motor in the transmission chain than the actual location of engagement between the gear drive and the transport device. The aforementioned stabilization is particularly useful in embodiments, in which the transport device comprises a bendable elongate element.

The first and second firing mechanisms may comprise a common trigger element and a second power-driven element for moving the trigger element. The trigger element may e.g. comprise a linearly displaceable member or a rotational member, such as a gearwheel. The control system of the biopsy device may be configured such that the first firing mechanism can be loaded and fired during a first movement segment of the trigger element, and so that the second firing mechanism can be loaded and fired during a second movement segment of the trigger element. For example, if the trigger element comprises a linearly displaceable member having a certain stroke, the first movement segment may correspond to a part of the stroke, and the second movement segment may correspond to a second part of the stroke. Alternatively, if the trigger element comprises a rotational element, the first movement segment may correspond to rotation of an initial angle of e.g. 90°, and the second movement segment may correspond to rotation of a subsequent rotation of e.g. another 90°.

The transport device and the first and second firing mechanisms may conveniently be powered or driven by one single motor such an electrical motor or pneumatic motor. It will thus be appreciated that first and second movement segments of the motor may be for loading the first and second firing mechanisms, respectively, whereas a further movement segment, e.g. rotation of another 170° of the trigger element, may be for movement of the sample-receiving device between the first extended position and the second retracted position.

It will thus be appreciated that the trigger element may be arranged with respect to the firing mechanisms and the transport device such that movement thereof in a first direction causes firing of at least one of the first and second firing mechanisms, and such that further movement of the trigger element in the first direction causes movement of the transport device to move the sample-receiving device from the first extended position to the second retracted position for ejection of a harvested tissue sample. This may e.g. happen during rotation of at most 360° of the trigger element, cf. the above example of angular ranges, which accumulate to 350°. Movement or rotation of the trigger element in a second direction, e.g. opposite rotation of opposite linear displacement, may cause movement of the transport device to move the sample-receiving device from the second retracted position to the first extended position for harvesting of a further tissue sample and/or for firing of a further double shot. The movement of the trigger element in the second direction may cause resetting of the first and/or second firing mechanisms to reset the mechanism(s) for a subsequent cycle of double and or single shots.

The control system of the biopsy device may comprise an electrically activated solenoid for causing an impart member of the first firing mechanism to move into a path of movement of the trigger element. For example, the trigger element may comprise a rotational wheel having an outwardly protruding element projecting from a surface thereof. When the solenoid has not caused the impart member of the first firing mechanism to move into the path of movement of the trigger element, the protruding element moves past the first firing mechanism without activating it during movement of the trigger element. Thus, only the second firing mechanism will be activated. If the solenoid is activated, however, the outwardly protruding element engages the impart member of the first firing mechanism, and movement of the trigger element will load and fire the first firing mechanism, before the second firing mechanism is possibly loaded and fired. It should be understood that the solenoid may, alternatively, be arranged to move the trigger element, so that its path of movement coincides with the impart member of the first firing mechanism.

In case the biopsy device is embodied as a hand-held unit, the first and second firing mechanisms may advantageously form part of the hand-held unit.

In one embodiment, the control system of the biopsy device is configured to operate the firing mechanisms and the transport device in a predefined cycle. Such a cycle may e.g. comprise the steps of:

optionally performing a double shot, if an operator of the device has initiated the double shot by providing a corresponding input to the control system, e.g. via an interface in the handle unit;

activating a vacuum pump optionally included in the device to aspirate or sever tissue into the cavity of the sample-receiving device;

performing a single shot to sever the tissue sample and interrupting vacuum suction prior to or subsequent to severing;

moving the sample-receiving device to the second retracted position;

ejecting the tissue sample from the sample-receiving device, e.g. by liquid flushing as described below;

returning the sample-receiving device to the first extended position.

The control system may e.g. be programmable or pre-programmed to perform other cycles, e.g. multiple repetition the steps of:

performing the single shot;

moving the sample-receiving device to the second retracted position;

ejecting the tissue sample from the sample-receiving device; and returning the sample-receiving device to the first extended position, so as to harvest a plurality of tissue samples without user intervention between the individual severing (i.e. single shot) operations.

The biopsy device may further comprise a control system for controlling movement of the transport device and for arresting the sample-receiving device in the second retracted position. The second retracted position is normally that position of the sample-receiving device, in which the at least one severed tissue sample may be ejected from the cavity of the sample-receiving device. In order to take the burden of arresting the sample-receiving device in the correct position off the physician operating the device, the aforementioned control system may thus be configured to automatically arrest the sample-receiving device in the second retracted position. In one embodiment, the control system comprises a sensor for detecting the position of the sample-receiving device and/or the cavity therein. For example, a photocell or an electromechanical switch may be provided for providing a signal to the control system, when the sample-receiving device is in or close to its second retracted position. Alternatively, or in addition, the control system may be arranged to automatically detect a distance between the first extended position and the second retracted position.

It will thus be appreciated that the control system may allow the biopsy device to automatically operate with different needles of different lengths, there being no need for configuration by the user of the device in order to adapt the control system to a specific needle length. In case the hollow needle and the sample-receiving device are comprised in a disposable unit, which is releasably attached to the handle unit of the device, exchange of the hollow needle with another one of different length is easily performed. Such exchange is further facilitated thanks to the ability of the control system to arrest the sample-receiving device in the second retracted position without specific user input being required for adapting the control system to a specific needle length, and the biopsy device is further rendered fail-safe with respect to correct positioning of the sample-receiving device in the second retracted position.

The control system may for example be configured to automatically detect a distance between the first extended position and the second retracted position of the sample-receiving device upon attachment of the disposable unit to the handle unit. Accordingly, the control system may be configured to detect placement or replacement of the disposable unit in the handle unit, e.g. by means of a sensor integrated in the handle unit, and, in response to such detection, initiate the aforementioned detection of the distance between the two positions.

In order to achieve the detection, the disposable unit may comprise an electronic memory, and the handle unit may comprise an electronic interface for deriving information stored in the electronic memory, the electronic interface being configured to communicate the information to the control system. It should be understood that the ability of communicating between a disposable unit and further elements of the biopsy device, e.g. the handle unit, constitutes and independent aspect of the present invention, which may benefit from, but which does not require the presence of other features disclosed herein. For example, the unit accommodating the control system may be a hand-held or non-hand unit. The electronic memory may e.g. comprise a three of four terminal serial EEPROM, EPROM or ROM containing terminals ground, Vdd, CLK and bi-directional data line, such as a serial EEPROM ATMEL AT24C01. The information stored in the electronic memory may e.g. represent a distance between the first extended and the second retracted position of the sample-receiving device, a length of the outer hollow needle and/or a length of the bendable elongate element.

As an alternative or supplement to the electronic memory, the control system may comprise a sensor for detecting when the sample-receiving device reaches a proximal extremity of its movement range, the movement range being preferably predefined. The proximal extremity may for example be the second retracted position or a position at a predefined distance from the second retracted position, which predefined distance is independent of the length of the needle, i.e. which does not change when the disposable unit is exchanged. A distal extremity of the sample-receiving device may e.g. be the first extended position. The sensor for detecting the arrival of the sample-receiving device at the proximal extremity may e.g. detect a change in a physical characteristic, for example the change of electrical current or voltage, magnetic field, or the change of an acoustic, optical or mechanical parameter. The sensor may comprise a Hall sensor, potentiometer, current measuring device or a mechanical switch.

For example, the transport device may comprise a position or movement signal generator for generating a position or movement signal to the control system indicative of the longitudinal position or movement of the sample-receiving device. In this embodiment, the control system is configured to, upon mounting of the hollow needle and the sample-receiving device to the handle unit:

activate the transport device to retract the sample-receiving device to its proximal extremity and to record the position or movement signal in the proximal extremity; and to utilize the recorded position signal as a position reference point for subsequent arresting of the sample-receiving device in the second retracted position following tissue harvesting.

Preferably, a driving force is transmitted to the transport device from a motor, which is controlled by a microcontroller, the microcontroller receiving the position or movement signal as an input, in dependency of which input an output for the motor is generated.

To achieve the desired position control of the sample-receiving device, the control system may comprise at least one pulse-emitting device, such as a Hall element, for producing pulses in dependency of the movement or position of the sample-receiving device. The proximal extremity of the sample-receiving device may be defined by a mechanical stop for the sample-receiving device, conferring a change in the production of pulses when the sample-receiving device makes contact with the mechanical stop.

In case the transport device receives a driving force from an electrically driven motor, the sensor may, as an alternative or supplement to the Hall element, comprise a current or voltage sensor for measuring motor current passing through the motor. Accordingly, a rise of motor current beyond a predefined threshold value may be used as an indicator that the sample-receiving device has reached its proximal extremity, e.g. a mechanical stop.

The aforementioned position signal generator may comprise a potentiometer, the potentiometer being e.g. arranged at a transmission axle for transmitting a driving force to the transport device.

Upon mounting of the disposable unit to the handle unit, the control system may perform an initial run or calibration cycle to move the sample-receiving device to its distal and/or proximal extremity to determine the length of the needle, the distance between the first extended and the second retracted position of the sample-receiving device or any other value, which may render the control system capable of arresting the sample-receiving device in the second retracted position. The initial run preferably returns the sample-receiving device to a default position, e.g. the first extended position.

The handle unit, the hollow needle, the sample-receiving device, the transport device and the control system and optionally all other components of the present biopsy device may be comprised in a hand-held unit.

In a second, independent aspect, the present invention provides a disposable unit for a biopsy device for harvesting at least one tissue sample from a body of a living being, the disposable unit comprising:

a hollow needle with a distal end portion adapted to be introduced into the body;

a cutting mechanism for severing the at least one tissue sample;

a sample-receiving device with a cavity for receiving the at least one severed tissue sample, the sample-receiving device being receivable in the hollow needle and movable therein;

a transport device for moving the sample-receiving device in the hollow needle, the transport device comprising a bendable elongate element;

an interface for connecting the disposable unit to an external unit, a unit which is external of the disposable unit, the external unit comprising a driving unit with a power source, the interface being adapted to transmit a driving force of the driving unit to the transport device. The external may e.g. comprise the handle unit as described above.

As it will have become apparent from the previous parts of the description, the disposable unit may further comprise a coiling device for coiling up the bendable elongate element.

In a third, independent aspect, the invention provides a biopsy device for harvesting at least one tissue sample from a body of a living being, the device comprising:

a hollow needle with a distal end portion adapted to be introduced into the body, and first orientation means;

a cutting mechanism for severing a tissue sample;

a sample-receiving device with a cavity for receiving the severed tissue sample, and second orientation means, the sample-receiving device being receivable in the hollow needle and movable therein between a first extended position and a second retracted position;

a transport device for moving the sample-receiving device in the hollow needle;

wherein the first and second orientation means co-operate to orient the sample-receiving device in a plane perpendicular to an axis of movement of the sample-receiving device.

Such orientation means are described in more detail above in connection with the first aspect of the invention.

BRIEF DESCRIPTION OF THE DRAWINGS

An embodiment of the invention will now be described with reference to the drawings, in which.

Figure 1:
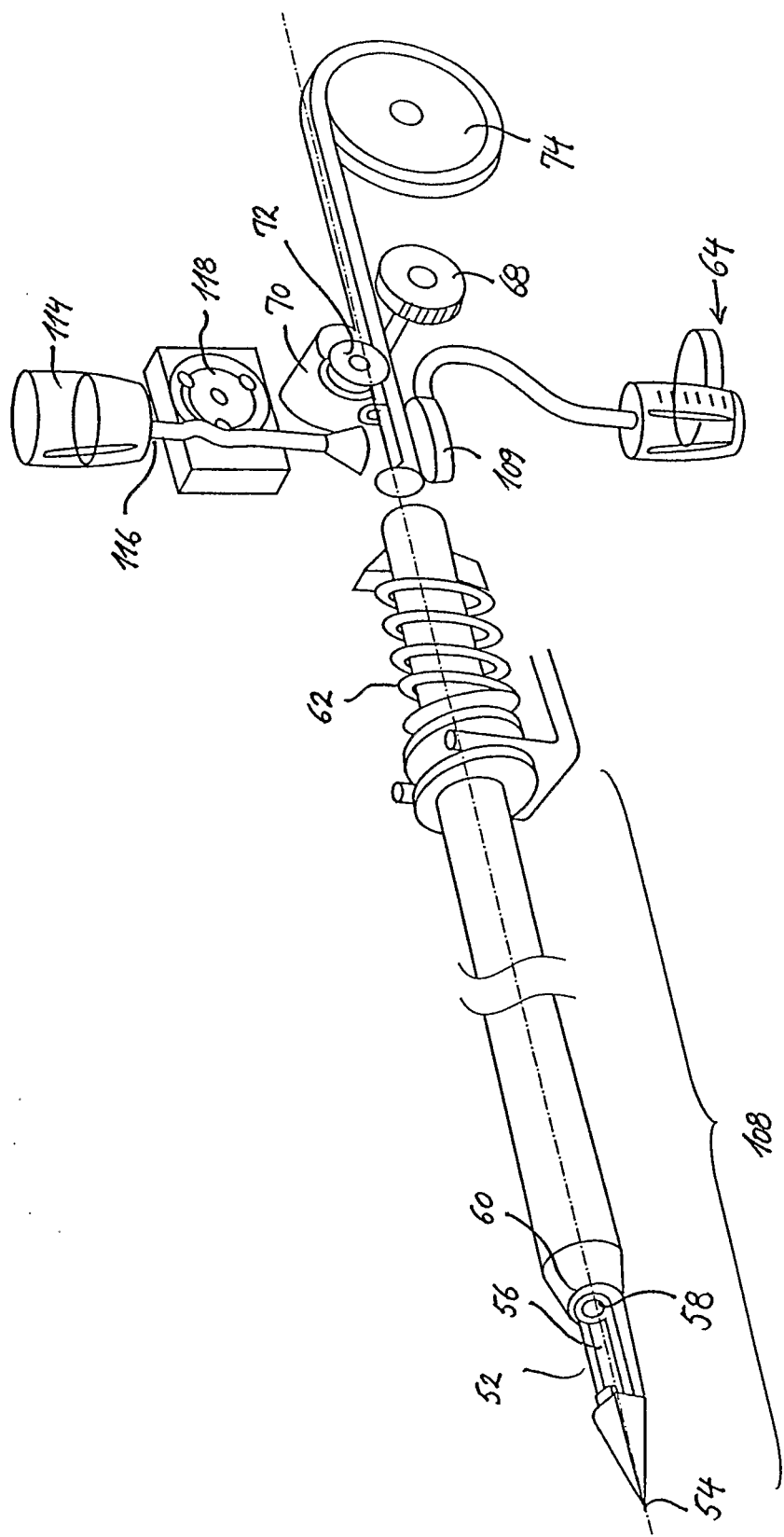
FIG. 1 is a general illustration of a biopsy device.

While the invention is susceptible to various modifications and alternative forms, specific embodiments are shown by way of example in the drawings and are described in detail herein. It should be understood however, that the invention is not intended to be limited to the particular forms disclosed.

DETAILED DESCRIPTION OF THE DRAWINGS

FIG. 1 shows a simplified schematic illustration of a biopsy device incorporating features of the present invention. The device includes biopsy needle 108 comprising a hollow needle 50, in which there is arranged a longitudinally movable tissue sample-receiving device 52. The sample-receiving device comprises a tapered distal tip 54 and a cavity or canoe 56 for receiving a tissue sample. The sample-receiving device comprises a vacuum port 58, which is in fluid communication with the canoe 56 to allow tissue to be sucked into the canoe once the canoe is placed at a suspect site within the body of a living being. Vacuum is provided by a vacuum pump (not shown). A distal end portion of the hollow needle 50 provides a circumferential cutting edge 60 for severing the tissue sample sucked into the canoe 56. The device comprises a spring-loaded firing mechanism, which in FIG. 1 is schematically illustrated by a spiral spring 62, the firing mechanism being arranged to displace the hollow needle 50 in a forward (distal) direction to sever the tissue sample sucked into the canoe 56. At a proximal end of the device, there is provided a sample flushing chamber 109, from which the severed tissue sample in the canoe 56 can be ejected into a sample container 64. More specifically, the sample-receiving device 52 with the canoe 56 is retracted from a first extended position, in which the canoe 56 projects from the distal end of the hollow needle 50 as shown in FIG. 1, to a second retracted position, in which the canoe 56 is aligned with upper and lower openings in the sample flushing chamber 109. A flushing liquid, such as saline, is applied to eject the tissue sample from the canoe 56 into the sample container 64, the flushing liquid being conveyed from a liquid container 114 via a hollow liquid transport member or tube 116 by the aid of a peristaltic pump 118.

In order to move the sample-receiving device 52 with the canoe 56 between the first extended position shown in FIG. 1 and the second extracted position, there is provided a transport device comprising a bendable elongate element 66 in the form of a bendable bar or wire. A lower surface of the bendable bar or wire is toothed, so that it may engage a rotatable gear wheel or pinion 68 arranged to longitudinally displace the bar or wire 66 to thereby move the sample-receiving device 52 backward and forward in the hollow needle 50. A motor 70 is provided to impart a driving force on the gear wheel or pinion 68, and a guiding wheel 72 is provided to stabilize the bendable, flexible bar or wire 66. In order to control the bar or wire 66 when the canoe 56 is retracted for tissue sample ejection, there is provided a coiling device 74 for the bar or wire 66.

The biopsy device schematically illustrated in FIG. 1 is operated as follows: initially, the sample-receiving device 52 and the hollow needle 50 are arranged, such that the sample receiving cavity or canoe 56 is covered by the hollow needle 50, i.e. such that the outer surface of the tapered distal tip 54 of the sample-receiving device 52 forms a tapered distal continuation of the outer surface of the hollow needle 50. In this configuration, the needle 108 is caused to penetrate body tissue of a patient, for example through manual insertion into the patient's body by a physician. Once the needle has penetrated a suspect tissue mass, e.g. a tumour, the hollow needle 50 is retracted to the position shown in FIG. 1, thereby compressing the spring 62 and thus loading the firing mechanism for the hollow needle. Vacuum is then applied through vacuum port 58 to suck tissue into the canoe 56. The firing mechanism for the hollow needle 50 is subsequently released, and the hollow needle 50 is fired forwardly, i.e. in a distal direction, to its initial position, in which it covers the canoe 56. This forward firing brings about the result that the circumferential cutting edge 60 of the hollow needle severs the tissue sample in the canoe 56. The sample-receiving device 52 is then retracted to its second retracted position, in which the canoe 56 is aligned with the sample flushing chamber. Movement of the sample-receiving device is caused by rotating the gear wheel 68 in a clockwise direction, the gear wheel 68 engaging the flexible bar or wire 66, which in turn is attached to the sample-receiving device 52. In the retracted position of the canoe 56, a flow of flushing liquid is forced to pass through the sample flushing chamber to eject the tissue sample from the canoe into the sample container 64. Once ejection has been completed, the flow of flushing liquid is interrupted, and the gear wheel 68 is rotated counter clockwise to cause the flexible bar or wire 66 to be displaced in a distal direction, whereby the sample-receiving device 52 is pushed back to its first extended position. The above described cycle including tissue sample harvesting and ejection may then be repeated one or more times to obtain several tissue samples without retracting the hollow outer needle 50 from the suspect site in the body.

It should be understood that the elements provided at the proximal end of the biopsy device shown in FIG. 1, i.e. the firing mechanism including spring 62, gear wheel or pinion 68, motor 70, guiding wheel 72, coiling device 74, optionally the sample container 64, sample flushing chamber 109, liquid container 114, tube 116, pump 118, and vacuum pump (not shown) may be conveniently integrated in a handle unit as elaborated in the below-appended description of embodiments of the invention.

Figure 2:
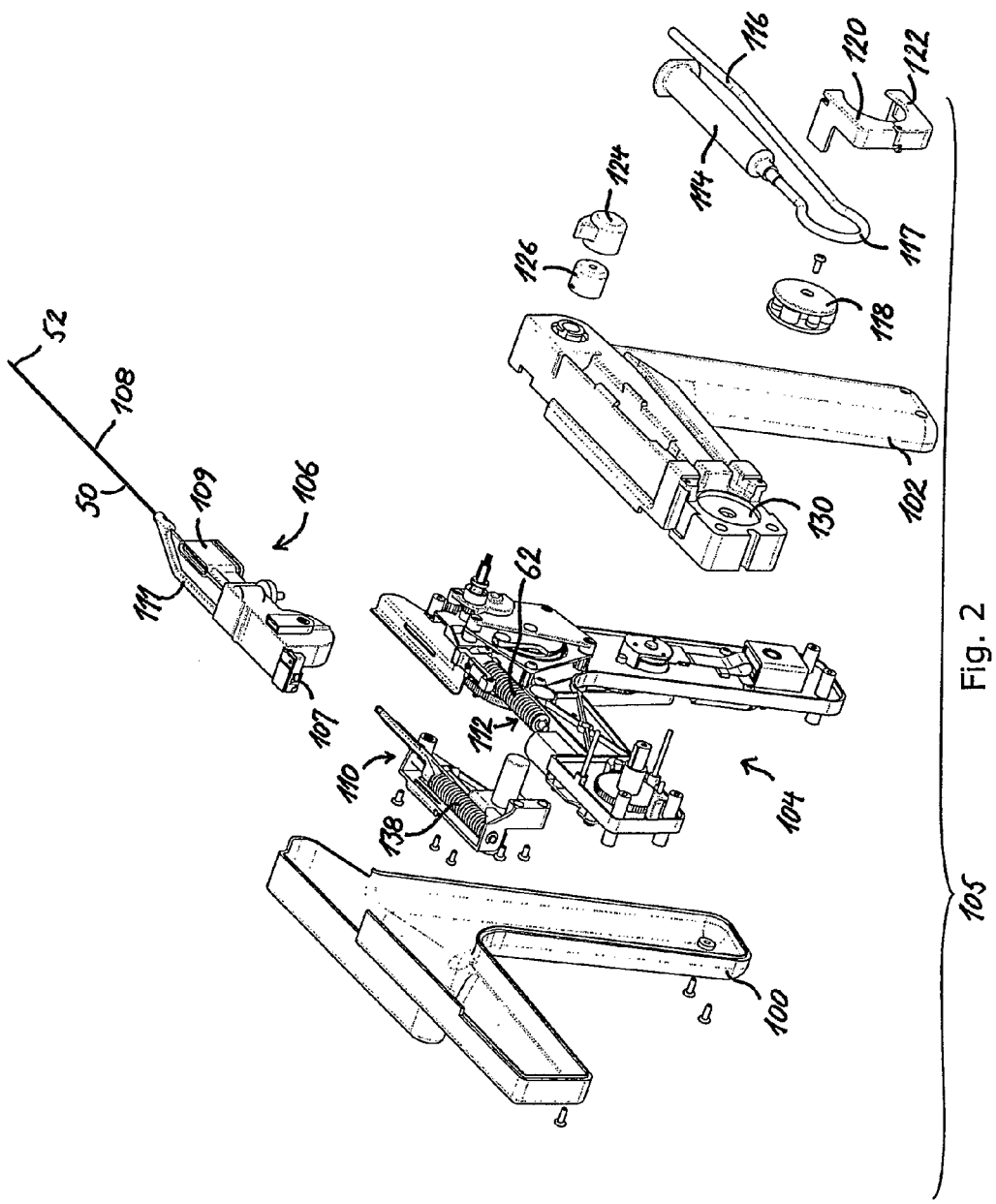
FIG. 2 is an exploded view of an embodiment of the biopsy device.

FIG. 2 is an exploded view of an embodiment of a biopsy device according to the present invention. The device comprises a left cover part 100 and a right cover part 102 and, interposed between the cover parts, a gear chassis unit 104 and a disposable unit 106 including a biopsy needle 108 and a sample flushing chamber 109. There is further provided a first firing mechanism 110 for firing the biopsy needle in a first mode as explained in detail below. The first firing mechanism 110 forms an integrated unit, which is optional in the present biopsy device. The gear chassis unit 104 includes a second firing mechanism 112 for firing the biopsy needle in a second mode as explained in detail below. The right cover part 102 is formed to accommodate a flushing system for conveying liquid to the disposable unit 106 in order to eject a body tissue sample from the sample flushing chamber 109. The flushing system includes a liquid container 114, to which there is connected a hollow liquid transport member or tube 116, the tube defining a bent portion 117. In order for liquid to be conveyed from the container 114 to the sample flushing chamber 109 through the tube 116, there is provided a peristaltic pump 118 for engaging the bent portion 117 of the tube 116. When mounted in the right cover part 102, the bent tube portion 117 is held firmly against the peristaltic pump 118 by means of a pair of jaws 120, 122. When assembled, the left and right cover parts 100, 102, the gear chassis 104 and the flushing system 114-122 forms a handle unit 105, to which the disposable unit 106 is releasably securable. A locking knob 124 comprising an internal bushing 126 is provided to releasably secure the disposable unit 106 to the handle unit 105.

Figure 3:
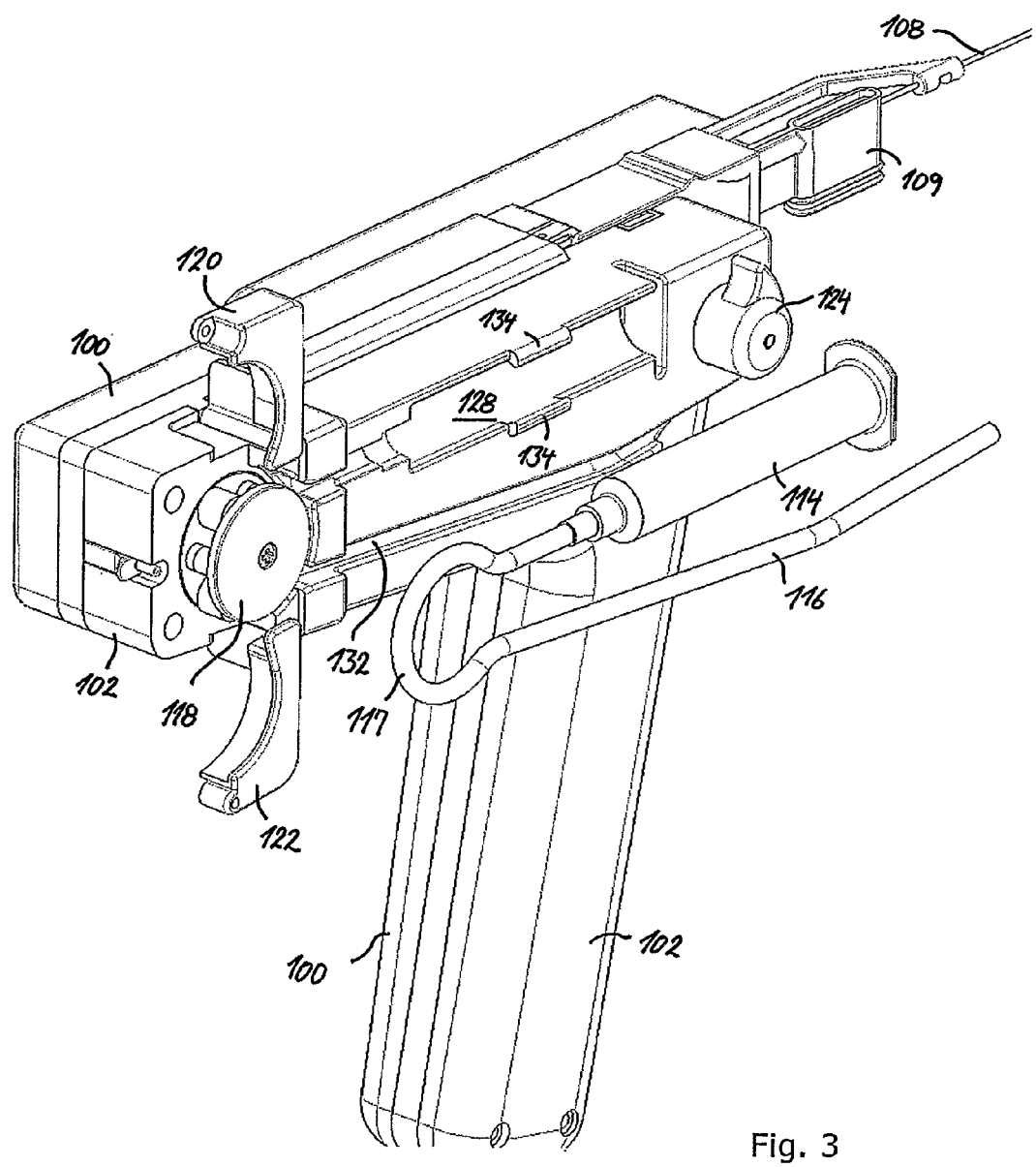
FIGS. 3-6 illustrate a liquid flushing system in the biopsy device.
Figure 4:
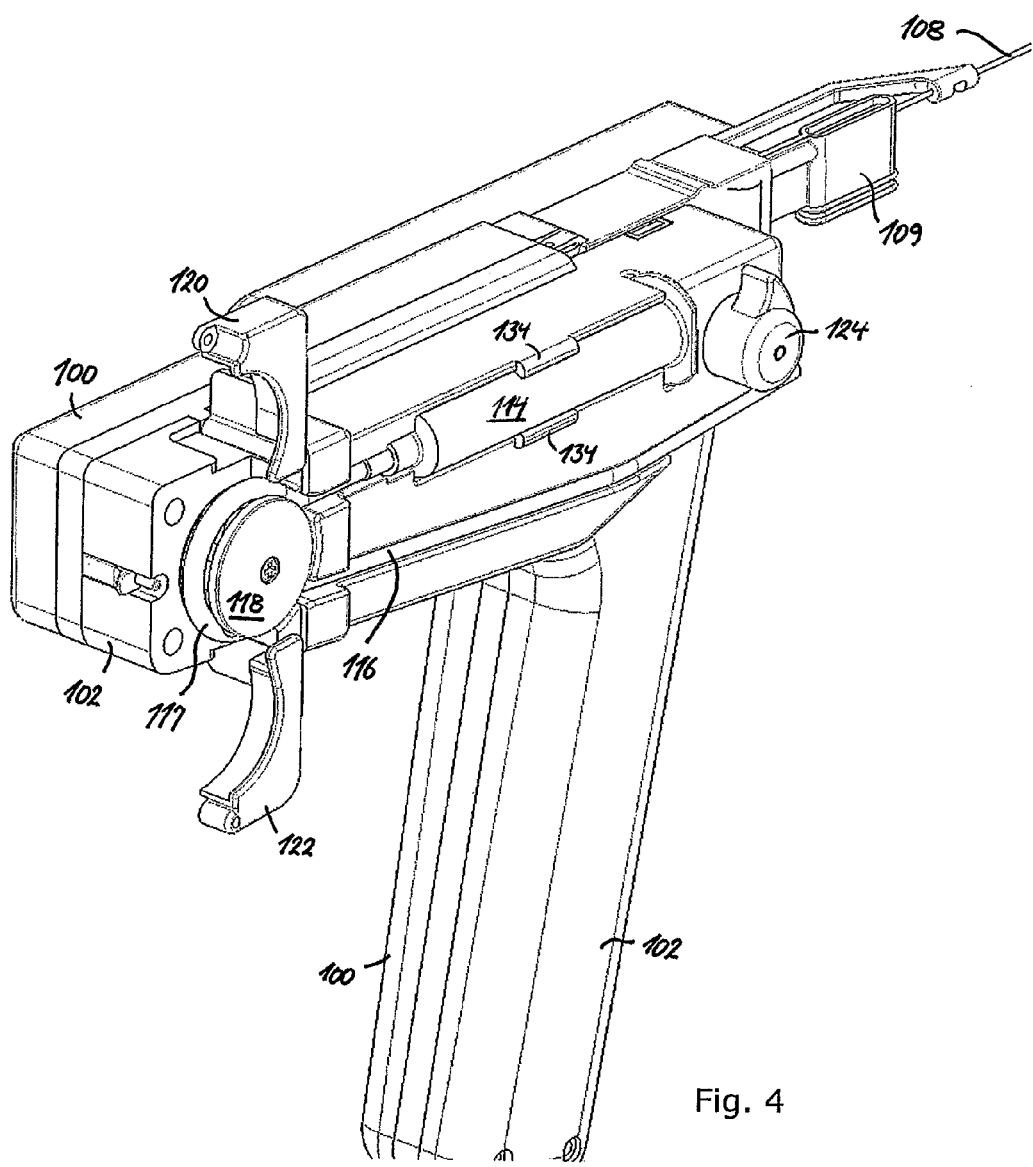
Figure 5:
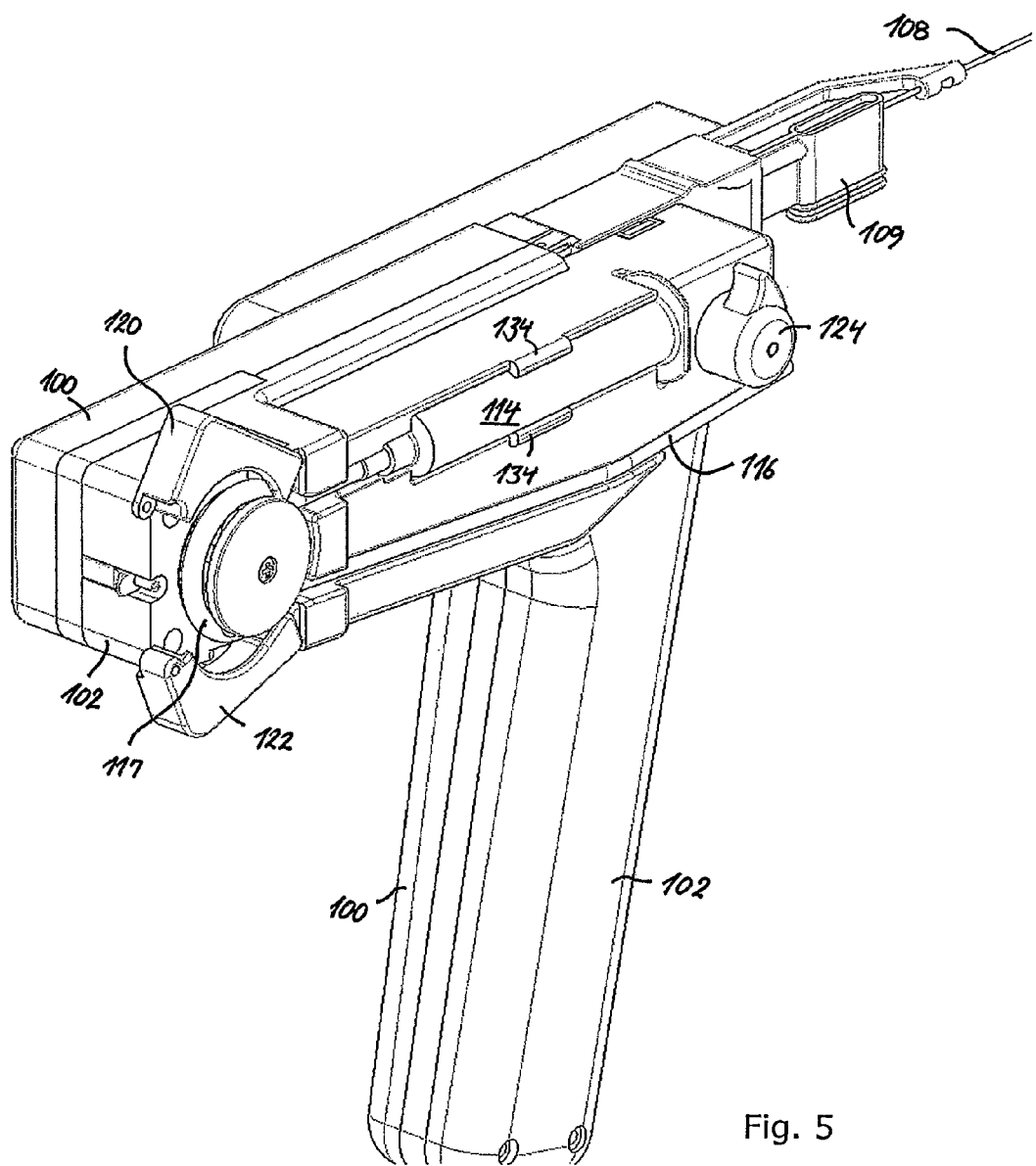
Figure 6:
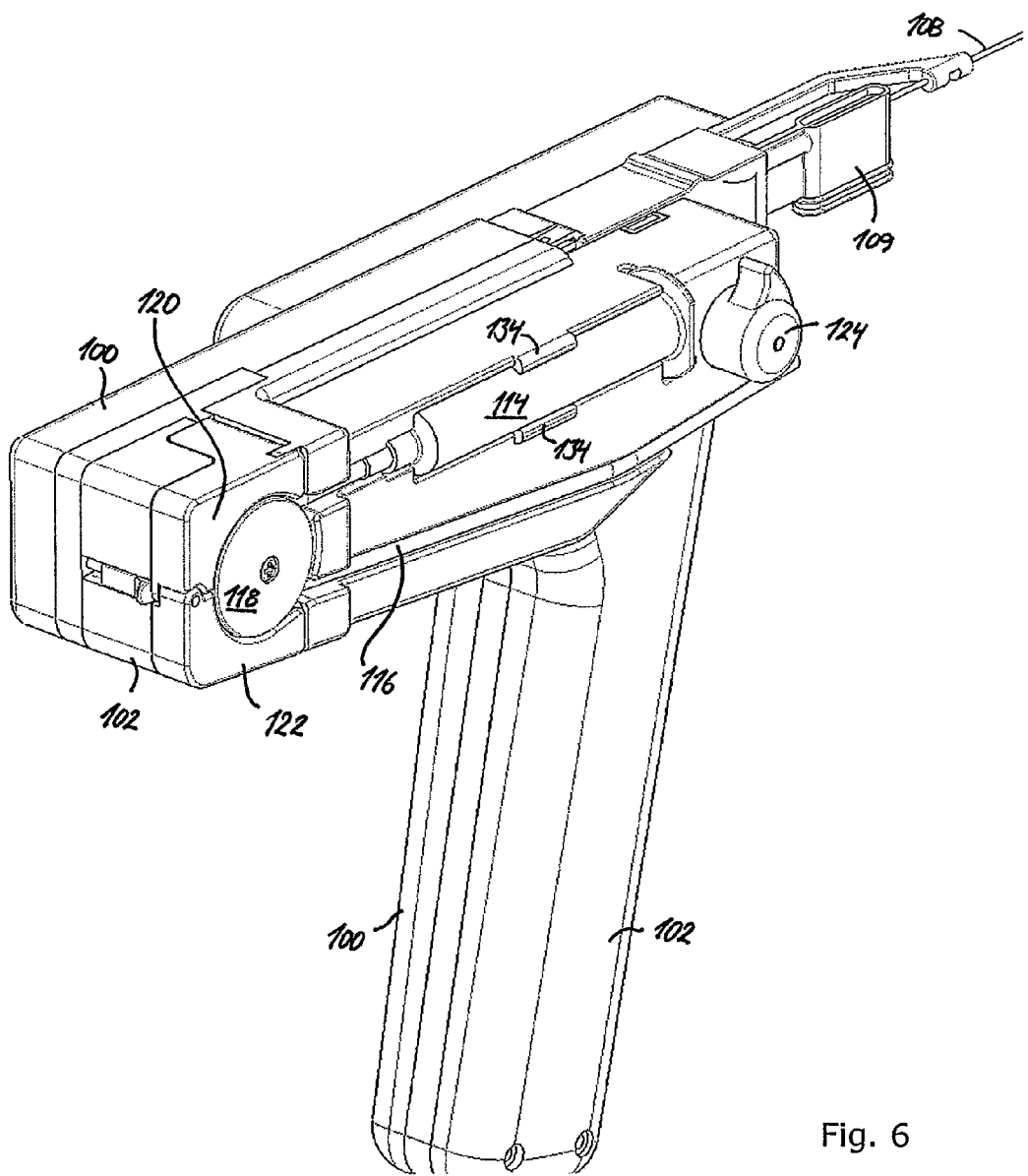

The liquid flushing system is disclosed further in FIGS. 3-6. In the external surface of right cover part 102, there is provided indentations 128, 130 (see FIG. 2) and 132 for receiving the liquid container 114, the peristaltic pump 118 and the tube 116, respectively. A pair of projections 134 is provided at upper and lower edge portions of indentation 128 to secure the container in the indentation 128. The liquid container 114 and the tube 116 are disposable elements, which an operator of the biopsy device may exchange on a regular basis. Exchange of these elements do not require removal of the pump 118, which normally remains attached to the right cover part 102 during exchange of the container 114 and tube 116. In FIG. 3, the jaws 120, 122 are open, and the container 114 and the tube 116 are ready to be placed in the corresponding indentations 128, 130 and 132 formed in the right cover part 102. FIG. 4 illustrates the container 114 and the tube 116 accommodated in the right cover part, with the bent tube portion 117 adequately placed around the circumference of the pump 118. In FIG. 4, the jaws 120 and 122 are open, whereas in FIG. 5, the jaws are partially pivoted to their closed position, and in FIG. 6 the jaws 120, 122 are fully pivoted to their closed position, in which they keep the bent tube portion 117 in close contact with the pump 118. When the container 114 and tube 116 are thus mounted in the right cover 102, the free end of tube 116 is connected to a conduit in the disposable unit 106 (cf. FIG. 2) for providing a fluid path from the container 114 to the sample flushing chamber 109 of the disposable unit.

Figure 7:
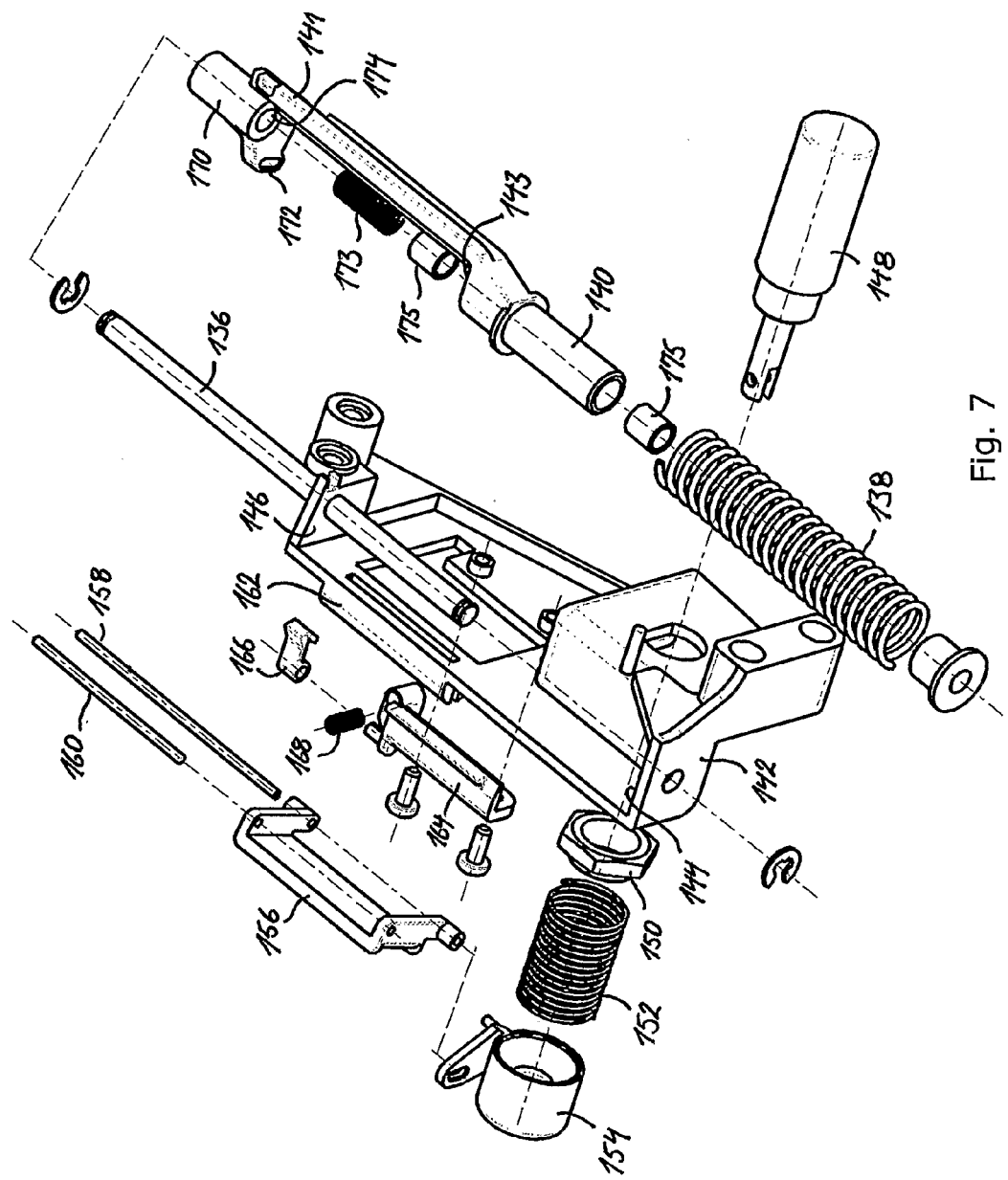
FIGS. 7-25 illustrate a first firing mechanism for firing an outer needle and a sample receiving device of a biopsy device essentially simultaneously.

The first firing mechanism 110 generally illustrated in FIG. 2 will now be further described with reference to the exploded view of FIG. 7. The firing mechanism 110 is arranged to fire the sample-receiving device 52 and the outer needle 50 of the biopsy device substantially simultaneously. Referring back to FIG. 1, the sample-receiving device 52 and the outer hollow needle 50 may thus be fired substantially simultaneously. Such simultaneous firing is useful for penetrating a suspect tissue mass, e.g. a tumour, penetration of which may be difficult due to e.g. hardness or due to a loosely supported attachment of the suspect tissue mass to surrounding tissue of the body. The loosely supported attachment may cause the suspect tissue mass to displace by pressure from the tip of the biopsy needle and to slide past the suspect tissue mass without penetrating it. It has been found that, by firing the inner and outer needles substantially simultaneously at a relatively high speed, it is possible to contact and penetrate even a loosely supported tissue mass. Below, the feature comprising substantially simultaneous firing of the outer needle and the sample-receiving device will be referred to as a "double shot".

The method of operation of the double shot firing mechanism 110 of FIG. 7 will be described below with reference to FIGS. 8-26. The mechanism comprises a primary axle 136 extending longitudinally through and parallel to a longitudinal axis of compression spring 138 and through a glider 140. A double shot frame 142 supports the spring 138 and the glider 140 between opposing wall sections 144, 146. This is also visible in FIG. 2, from which it is also apparent that the free end 141 of glider 140 extends into the disposable unit 106 through opening 107, the free end 141 engaging a yoke 182 (cf. FIG. 13), which in turn engages a needle driver 111 fixed to the outer surface of hollow needle 50. Below the spring 138, a solenoid 148 extends through the frame, on the opposing side of which the solenoid extends through a nut 150, compression spring 152 and into solenoid holder 154. The solenoid holder 154 engages a double shot lever 156 via a solenoid-connector axle 158 extending through the lever 156 and into the solenoid holder 154. An upper pivot pin 160 for the lever 156 is pivotally supported relative to the frame 142 and extends through frame projection 162, whereby solenoid 148 may cause the lever 156 to pivot around pivot pin 160. The double shot mechanism 110 further comprises a sliding rail 164, a sliding pawl 166, a spring pawl 168, and an impart member 170. Two through-going passages are provided in the impart member 170, a first passage 172 for the solenoid-connector axle 158, and a second passage 174 for the primary axle 136. An impart member return spring 173 is provided between the impart member 170 and a distally facing surface 143 of the glider 140.

Figure 8:
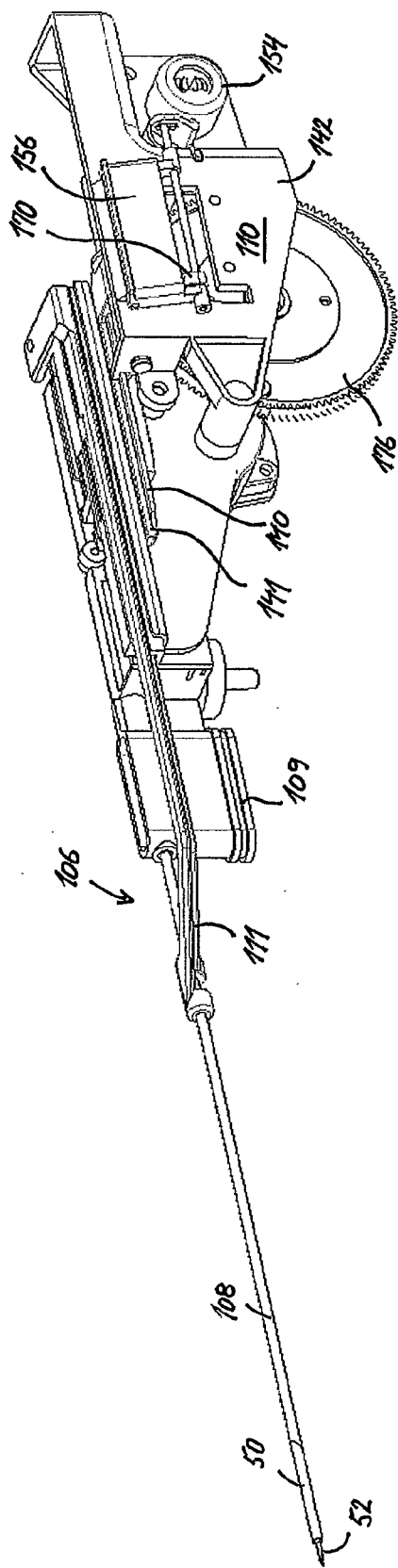

FIG. 8 includes structure of the biopsy device, which contributes to the double shot, i.e. substantially simultaneous firing of the outer, hollow needle 50 and the sample-receiving device 52. The double shot firing mechanism 110, illustrated in exploded view in FIG. 7, is assembled and mounted to the gear chassis unit 104 (cf. FIG. 2), the gear chassis unit 104 also supporting the disposable unit 106. In FIG. 8, the gear chassis unit is only partially shown for the sake of clarity. A motor-driven, toothed trigger wheel 176 is provided for causing compression of the compression spring 138 (cf. FIG. 7) as explained below with reference to FIGS. 11-17.

Figure 9:
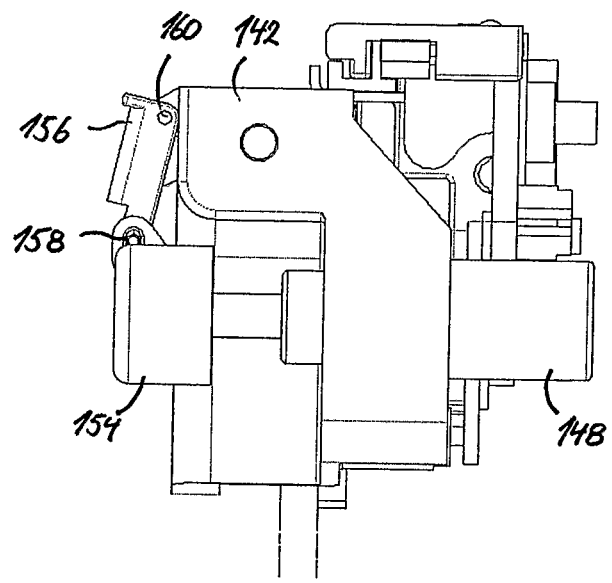
Figure 10:
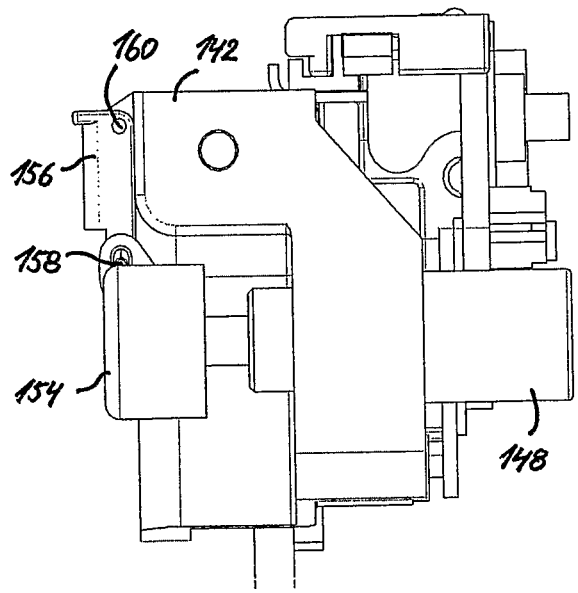

As shown in the end view of FIGS. 9 and 10, the lever 156 has two positions, an angled position as shown in FIG. 9, and a vertical position as shown in FIG. 10. The lever 156 is normally biased towards the angled position of FIG. 9 by the compression spring 152, the compression spring 152 being omitted in FIGS. 9 and 10 for the sake of clarity. In case an operator of the biopsy device intends to fire the outer, hollow needle 50 and the sample-receiving device 52 substantially simultaneously, i.e. to perform a double shot, an appropriate input is provided to an electronic control system of the biopsy device, e.g. via a keypad on an external surface of the cover 100, 102 (cf. FIG. 2). The double shot action commences by activation of the solenoid 148 to pivot the lever 156 around the upper pivot pin 160, whereby the lever is pivoted from the angled position of FIG. 9 to the vertical position of FIG. 10.

Figure 11:
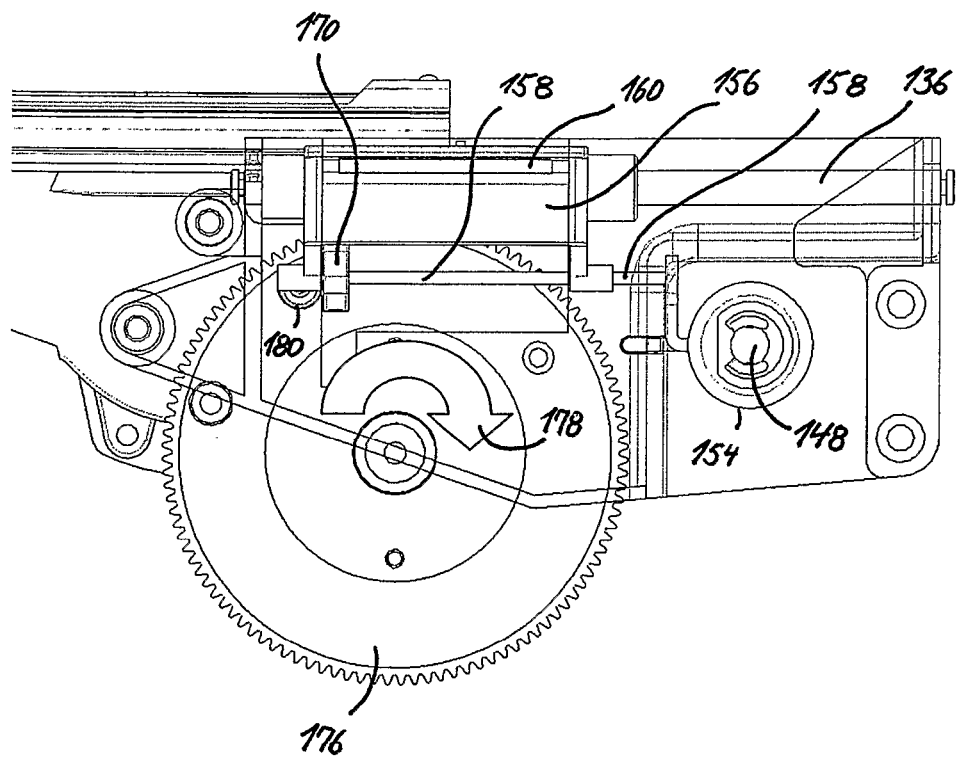

Subsequently, as shown in FIG. 11, the trigger wheel 176 is rotated in the direction of arrow 178. During the course of this rotation, a first bearing element 180 protruding from a surface of the trigger wheel 176 contacts the impart member 170, whereby the impart member 170 is displaced in the distal direction along the solenoid-connector axle 158. The stroke of the impart member 170 is defined by sidewalls of the lever. Thus, when the impart member 170 has arrived at the position shown in FIG. 12, further displacement thereof in the distal direction is not possible. As it will be described in detail below, this displacement of the impart member 170 causes the glider 140 (cf. FIG. 7), the needle driver 111 (cf. FIGS. 2 and 8) as well as outer, hollow needle 50 and the sample-receiving device 52 to be displaced in the distal direction, while the compression spring 138 is compressed, the thus compressed compression spring 138 being shown in FIG. 12 and omitted in FIG. 11. The firing mechanism for substantial simultaneous firing of the inner and outer needles is now loaded.

Figure 13:
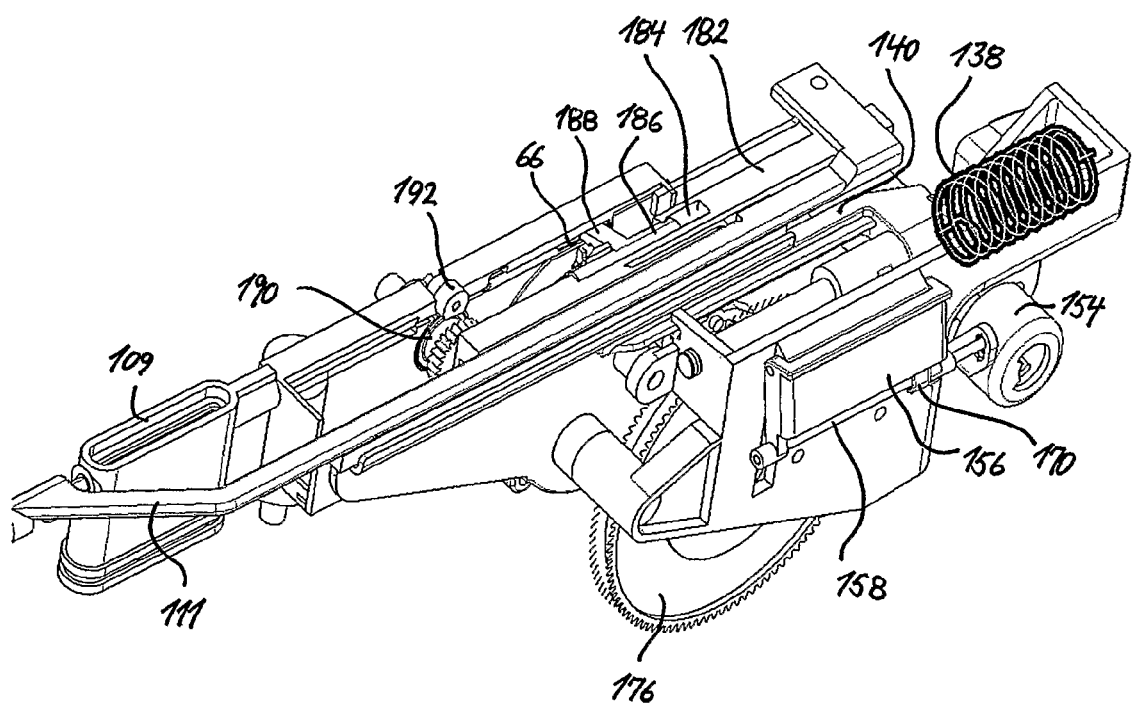

The loaded firing mechanism is illustrated in perspective view in FIG. 13. Compression spring 138 is loaded, and a yoke 182 has been moved to a proximal, i.e. retracted position shown in FIG. 13. The yoke 182 is connected to the glider 140 via a forcing pin 202 (cf. FIG. 18) engaging an indentation formed in the free end 141 of the glider 140, and the yoke 182 engages the needle driver 111, whereby rotation of the trigger wheel 176 in the direction of arrow 178 (cf. FIG. 11) causes the yoke 182 as well as the needle driver 111 and the outer needle 50 to be proximally displaced. The outer, hollow needle may thus be moved from its first extended position shown in FIG. 8 to its second retracted position of FIG. 13. As further illustrated in FIG. 13, the yoke 182 defines a recess 184, in which there is accommodated a slider 186, the slider 186 having an outwardly protruding centre piece 188. During retraction of the yoke 182, i.e. during loading of the double shot firing mechanism, the centre piece 188 is forced downwardly to engage the bendable elongate element 66, which is secured to the sample-receiving device 52. The required downward movement of the centre piece 188 is caused, as the centre piece 188, during proximal movement of the yoke engages an engagement member (not shown), which may, e.g. form part of a housing (not shown). Hence, when yoke 182 is moved in a proximal direction, the centre piece 188 is likewise displaced proximally, and in turn the bendable element 66 and the sample-receiving device 52 are moved along with the centre piece 188 of slider 186.

In the shown embodiment, the bendable element 66 comprises a toothed flexible wire or flexible rack, which is driven by an advancing gearwheel 190 (cf. FIG. 19) engaging teeth of the toothed flexible wire 66. Thus, rotation of the gearwheel 190 may cause the bendable elongate element 66 and the sample-receiving device 52 to be distally or proximally displaced, depending on the rotational direction of the gearwheel 190. A supporting roll 192 is provided for stabilizing the flexible wire 66, i.e. to prevent it from flexing upwardly, when it is moved in a distal direction to push the sample-receiving device 52 in the distal direction.

In one embodiment, the bendable elongate element 66 is made from Nylon 6-6. The bendable elongate element may have a generally circular cross section with flattened upper and lower surfaces, so that the element forms a wire with flat upper and lower surfaces and arc-shaped right and left surfaces. For example, the diameter of the element may be approximately 1.2 mm, with a cross-sectional dimension between the flattened upper and lower surfaces being approximately 0.85 mm. In one embodiment, the outer needle 50 has an outer diameter of approximately 2.1 mm and an inner diameter of approximately 1.8 mm, the outer diameter of the sample-receiving device 52 being, in that embodiment, approximately 1.8 mm, the inner diameter of the sample-receiving device being 1.5 mm.

Figure 12:
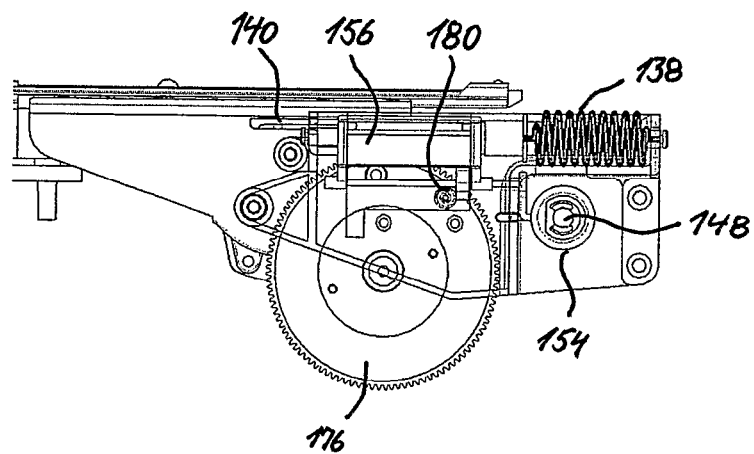
Figure 14:
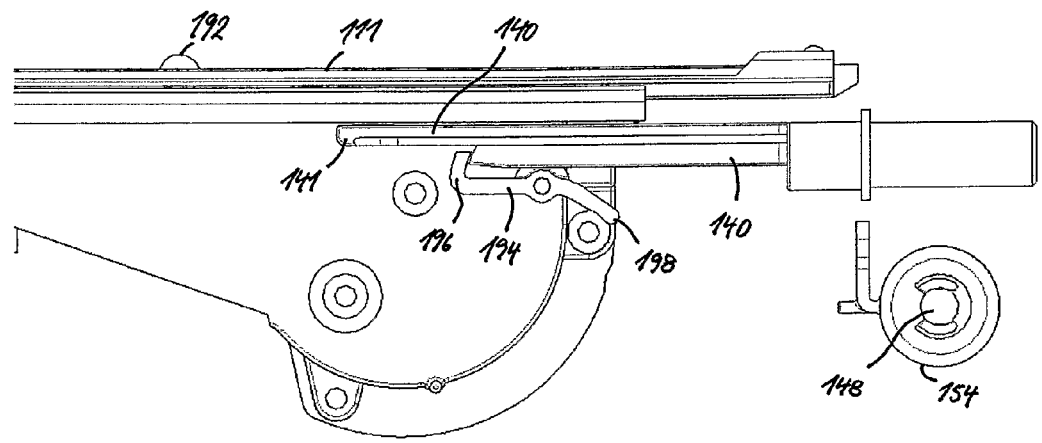

When the impart member 170 has been moved to its proximal extremity shown in FIGS. 12 and 13, a spring biased release hatch 194 defining a cam 196 engages a distally facing edge on the lower surface of the glider 140 as shown in FIG. 14. The release hatch 194 is not visible in FIGS. 11-13, as it is hidden behind the lever 156 and the trigger wheel 176. The release hatch 194 is rotationally spring biased, such that the cam 196 slides along the lower surface of the glider 140, until the impart member 170 and thus the glider 140 have reached their proximal extremity.

Figure 15:
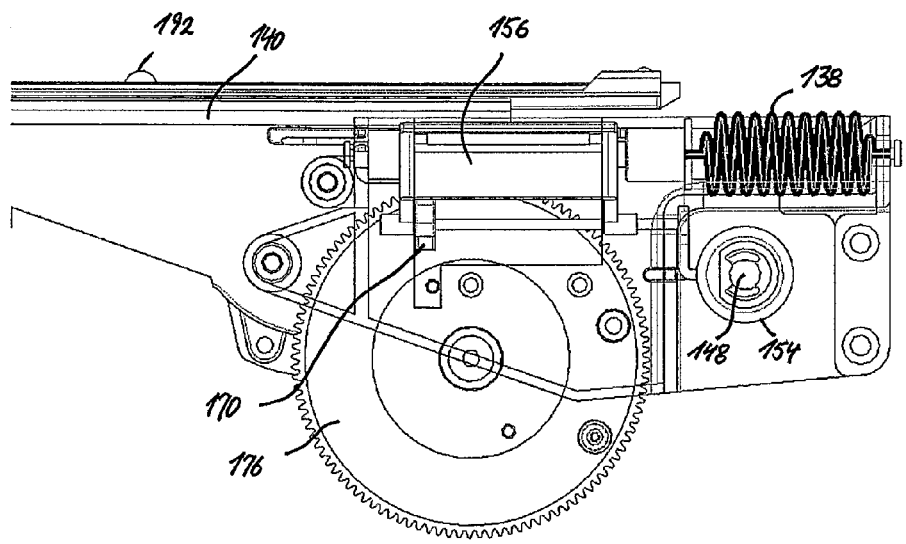

At this stage, rotation of the trigger wheel 176 is interrupted, and the solenoid 148 is deactivated, whereby compression spring 152 (cf. FIG. 7) returns the lever 156 to the inclined position shown in FIG. 9. In consequence, the first bearing element 180 (cf. FIGS. 11 and 12) looses contact with the impart member 170, and the impart member return spring 173 forces the impart member 170 back to its initial position, i.e. its distal extremity, as shown in FIG. 15. However, as the release hatch 194 engages the glider 140 as shown in FIG. 14, the spring 138 is kept loaded, and hence the glider 140, the yoke 182, the needle driver 111, the outer needle 50, the slider 186, the toothed flexible wire 66 and the sample-receiving device 52 are prevented from moving in the distal direction. The firing mechanism is now ready to fire, i.e. to release spring 138 to substantially simultaneously fire the outer needle 50 and the sample-receiving device 52.

Figure 16:
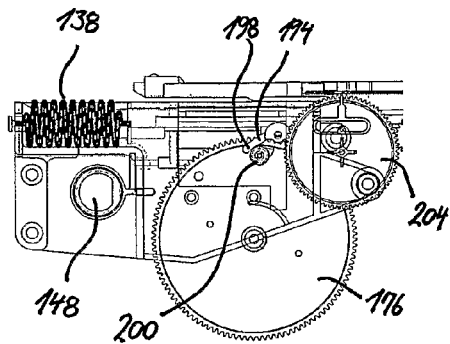
Figure 17:
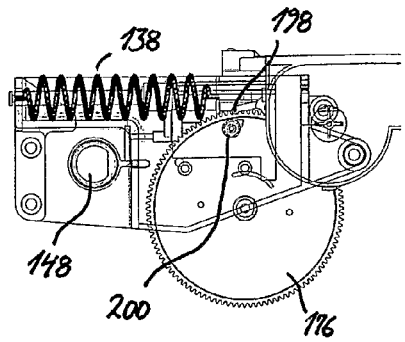
Figure 18:
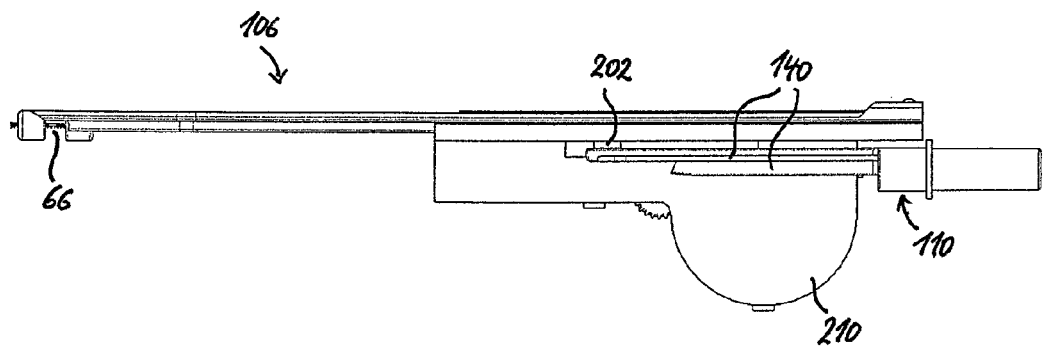
Figure 19:
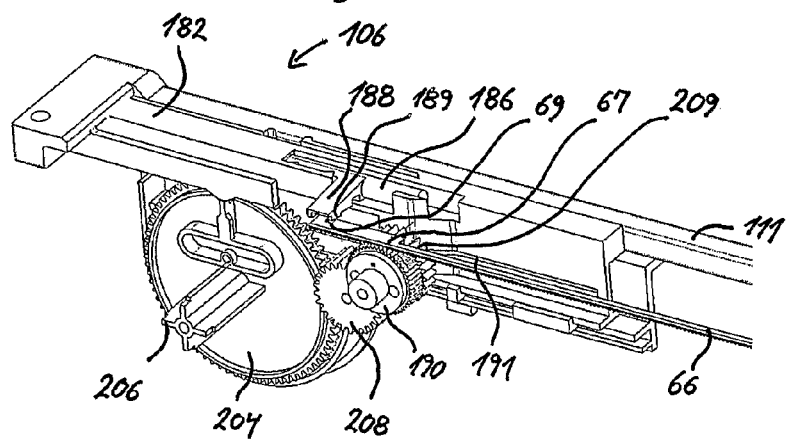

The side elevation views of FIGS. 16 and 17 show the device from a side opposite to the side viewed in FIGS. 11-15. Thus, the distal end of the device is to the left in FIGS. 16 and 17. Rotation of the trigger wheel 176 in the direction of arrow 178 (cf. FIG. 11) is now resumed, the trigger wheel thus rotating counter clockwise in FIGS. 16 and 17. A second bearing element 200 attached to the trigger wheel 176 now contacts a proximal portion of the release hatch 194, and the release hatch is thus caused to rotate clockwise in FIGS. 16 and 17 (counter clockwise in FIG. 14). As a result of this rotation, the cam 196 of the release hatch 194 moves downwardly, whereby its abutment against the glider 140 is released. The compression spring 138 is consequently released as illustrated in FIG. 17, and the double shot is fired.

In one embodiment of the invention, the compression spring 138 for the double shot is compressed by 20-25 mm during loading of the double shot mechanism as described above, corresponding to a 20-25 mm movement of the needle 50 and the sample-receiving device. Hence, in this embodiment, the needle 50 and the sample-receiving device 52 have been displaced 20-25 mm in the distal direction between the two positions shown in FIGS. 16 and 17, respectively.

The disposable unit 106, incorporating several of the elements described above in connection with the double shot firing mechanism, will now be further described with reference to FIGS. 19-26. The disposable unit 106 includes a driving gearwheel 204 for the toothed flexible wire 66. A cross-shaped driving axle 206 projects from a side surface of the driving gearwheel 204, the cross-shaped driving axle 206 engaging a correspondingly shaped member in the gear chassis 104 (cf. FIG. 2). The gear chassis 104 includes a motor for providing a driving force to the cross-shaped driving axle 206. The driving gearwheel 204 is arranged to drive an first intermediate gearwheel 208, which in turn is arranged to drive a second intermediate gearwheel 209, which drives the advancing gearwheel 190, the advancing gearwheel being arranged coaxially with the second intermediate gearwheel 209 in a plane adjacent the plane of the second intermediate gearwheel, whereby appropriate engagement portions are provided at opposing surfaces of the second intermediate gearwheel 209 and the advancing gearwheel 190. These engagement portions provide a releasable interconnection, so that, before the double shot is fired, the second intermediate gearwheel 209 is brought out of engagement with the advancing gearwheel 190. This disengagement is caused by an arm 191 forming part of the yoke 182, which consequently moves with the yoke. When the double shot has been fired, the second gear wheel 209 and the advancing gearwheel 190 return into mutual engagement. A proximal section 67 of the toothed flexible wire 66 is widened and includes a recess 69 for engagement by a flange portion 189 of the slider 186's centre piece 188. The housing element 210 shown in FIG. 18 houses a helical coiling-up groove for accommodating the toothed flexible wire 66 when the sample-receiving device 52 is retracted to its second retracted position, in which the canoe 56 is aligned with the flushing chamber 109 (cf. FIG. 2).

Figures 20, 22:
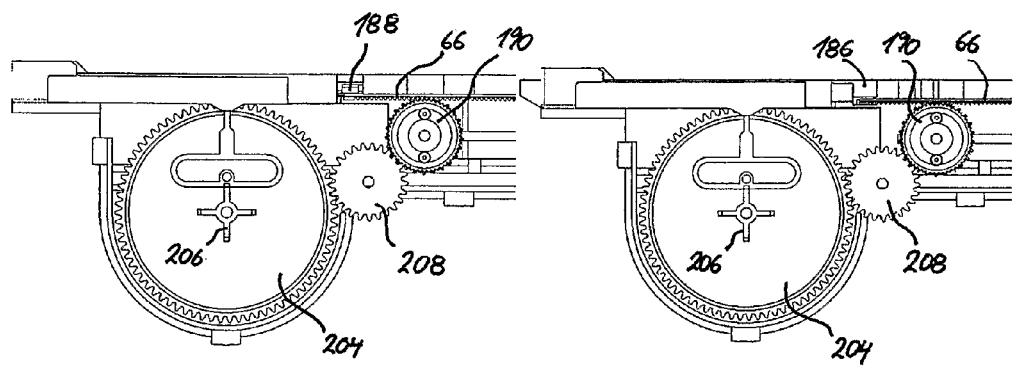
Figures 21, 23:
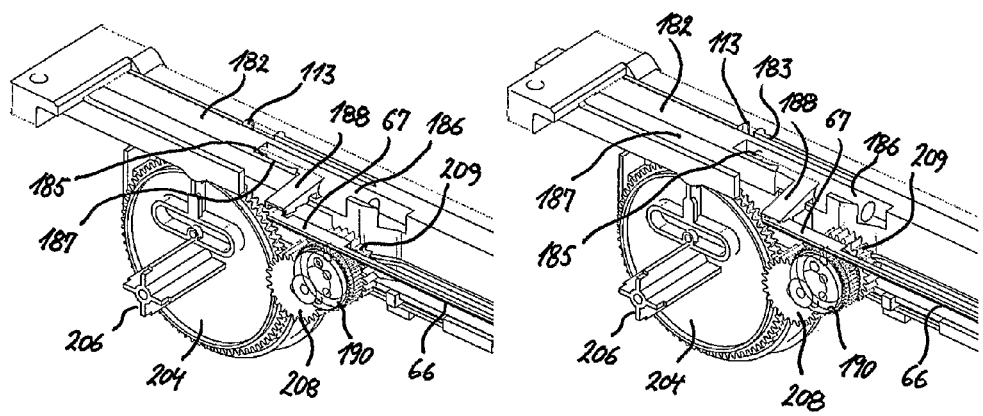

In FIGS. 20 and 21, the centre piece 188 of the slider 186 is lifted out of engagement with the widened proximal end portion 67 of the toothed flexible wire 66. In this mutual position of the elements, the toothed flexible wire 66 may be moved by providing a driving force to the cross-shaped driving axle 206 by an appropriate electrical motor (not shown), which advantageously may be integrated in the gear chassis 104. In FIGS. 22 and 23, the yoke 182 has been partly retracted as described above with reference to FIGS. 9-13, which has caused the centre piece 188 to engage the widened proximal end portion 67 of the toothed flexible wire 66. Upon further retraction of the yoke 182, a first yoke arm 183 engages a recess 113 in the needle driver 111, and a second yoke arm 187 engages a recess 185 in the slider 186, cf. also the top views of FIGS. 24 and 25.

Figure 24:
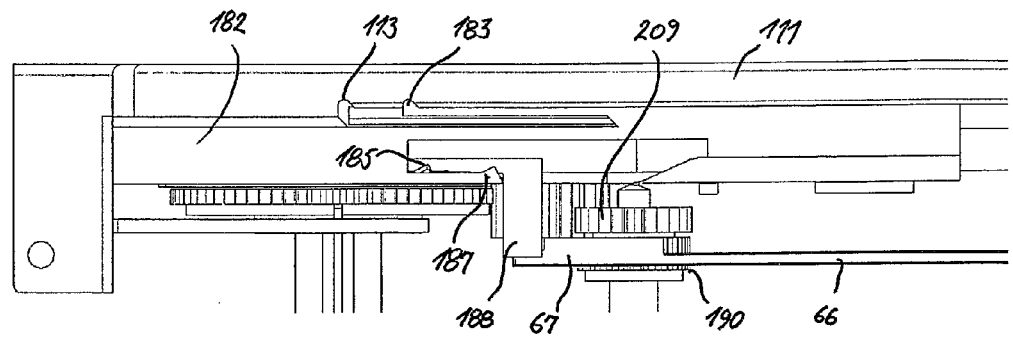
Figure 25:
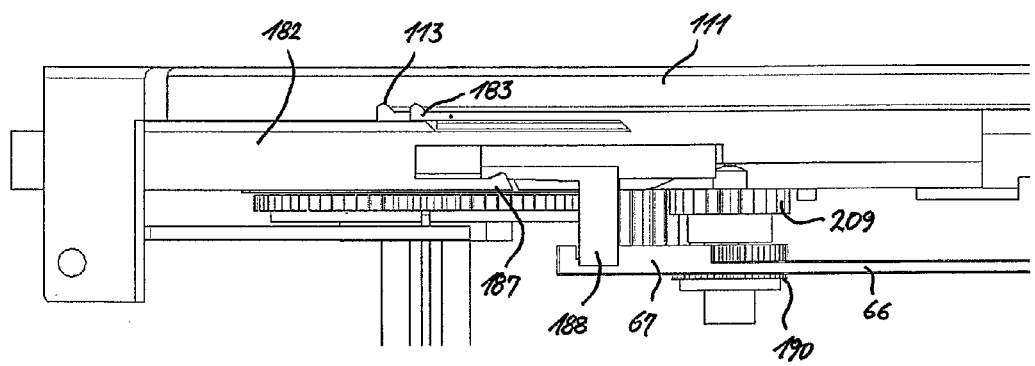

Following the centre piece 188's engagement with the widened portion 67 of the toothed flexible wire, but prior to retraction of the needle driver 111 and the toothed flexible wire 66 for loading of the double shot firing mechanism (cf. the above description of FIGS. 8-17), the second intermediate gearwheel 209 (cf. the above description of FIG. 19) is brought out of engagement with the advancing gearwheel 190 as illustrated in FIGS. 24 and 25, the second intermediate gearwheel 209 engaging the advancing gearwheel 190 in FIG. 24 and being out of engagement in FIG. 25. Accordingly, the driving gear mechanism for the flexible toothed wire 66 causes no resistance to the loading and releasing of the double shot firing mechanism. In an alternative embodiment, the advancing gearwheel 190 is kept in engagement with the wire 66 during loading and firing in order to stabilize the wire 66, i.e. to prevent flexing thereof. In such an embodiment, the first intermediate gearwheel 208 (cf. FIGS. 20-23) may advantageously be decoupled from the advancing gearwheel 190 in order to reduce resistance.

Figure 26:
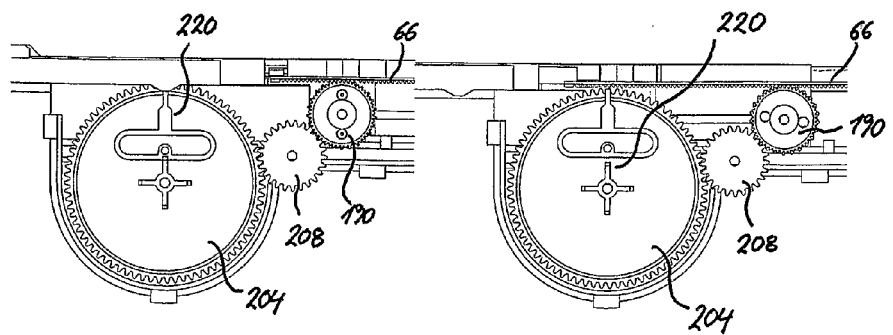
FIG. 26 illustrates a locking mechanism for a gearwheel of the firing mechanisms.

FIGS. 25 and 26 generally depict a locking mechanism 220 for locking the driving gearwheel 204 when the needle 50 is loaded for a single shot, cf. the description of FIGS. 27-31 below. As it will be understood, during the single shot, only the outer needle 50 is caused to be retracted and fired, while the position of the bendable elongate element 66 and the sample-receiving device 52 are locked or secured, as the locking mechanism 220 engages the cross-shaped driving axle 206.

Figure 27:
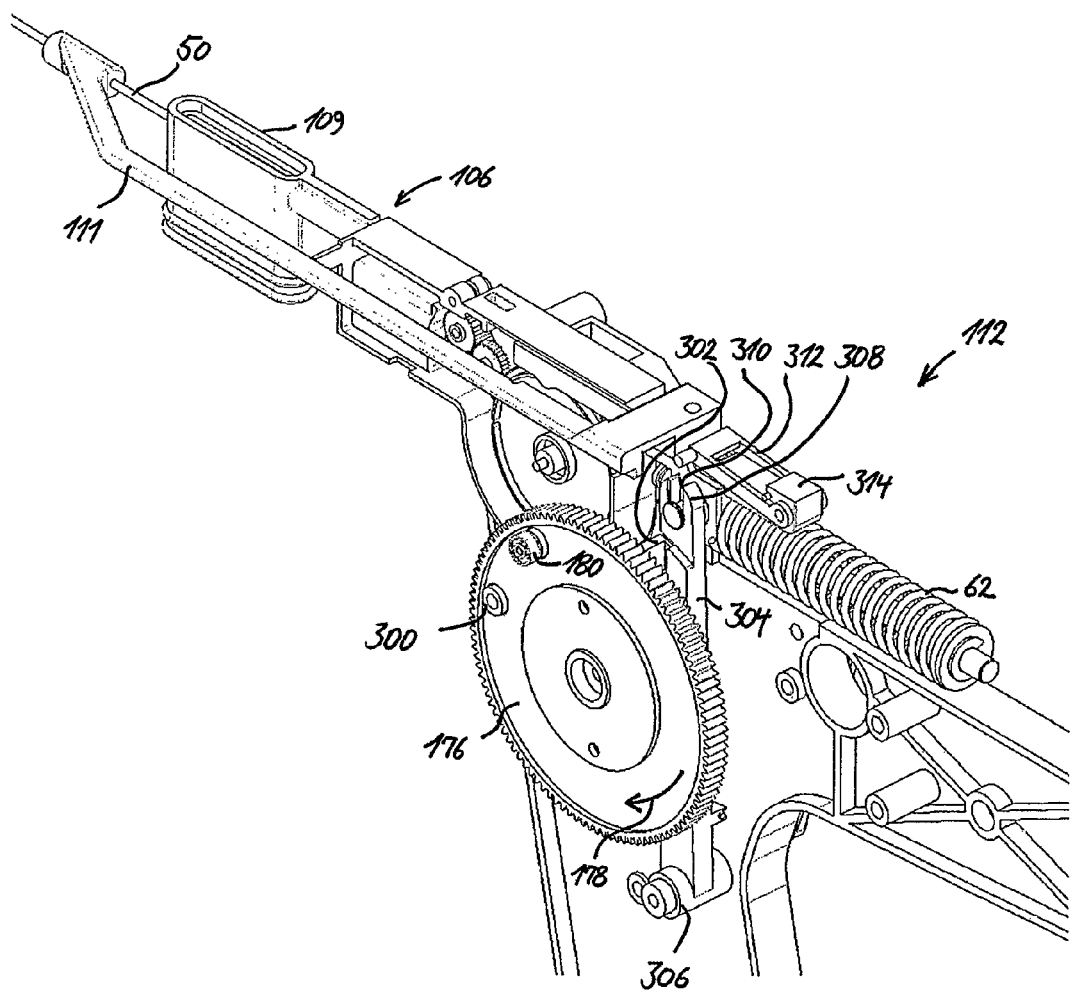
FIGS. 27-31 illustrate a second firing mechanism for firing only the outer needle.

The second firing mechanism, which causes the outer needle 50 with its distal circumferential cutting edge 60 (cf. FIG. 1) to be fired in the distal direction to sever a body tissue in the canoe 56 will now be further described with reference to FIGS. 27-31. It will be understood that only the outer needle 50 is fired, the sample-receiving device 52 remaining unaffected by firing of the second firing mechanism 112. This firing of the outer needle 50 will be referred to as "single shot" below. The trigger wheel 176 described above with reference to the double shot is also used in the single shot. In FIG. 27, the trigger wheel 176 is in the same position as depicted in FIG. 11. If the solenoid 148 is not activated and the double shot lever 156 is thus in the position of FIG. 9, rotation of the trigger wheel 176 in the direction of arrow 178 (cf. FIGS. 11 and 27) does not cause the first bearing element 180 to contact impart member 170 (cf. FIG. 11), as the impart member 170 is not in the plane of the bearing element 180. Consequently, the first firing mechanism, i.e. the firing mechanism for the double shot, is not loaded. The trigger wheel 176 accordingly rotates freely to the position of FIG. 28. If, alternatively, the solenoid 148 is activated and the double shot lever 156 is thus in the position of FIG. 10, rotation of the trigger wheel from the position of FIG. 27 to the position of FIG. 28 causes loading and of the double shot firing mechanism as described with reference to FIGS. 10-17. Once the trigger wheel has arrived to the position of FIG. 28, and the double shot firing mechanism has optionally been loaded and fired, a third bearing element 300 protruding from a side surface of the trigger wheel 176 opposite to the surface visible in FIG. 28 contacts an upright impart cam 302 attached to a trigger arm 304, the arm 304 being pivotally connected to the handle unit 105 (cf. FIG. 2) at a pivot 306. At its upper end, the trigger arm 304 forms a fork 308 engaging an transmission element 310, a proximal end of which abuts a distal end of the compression spring 62, and a distal end of which is connected to the needle driver 111 via a pivotally mounted element 312.

Figure 28:
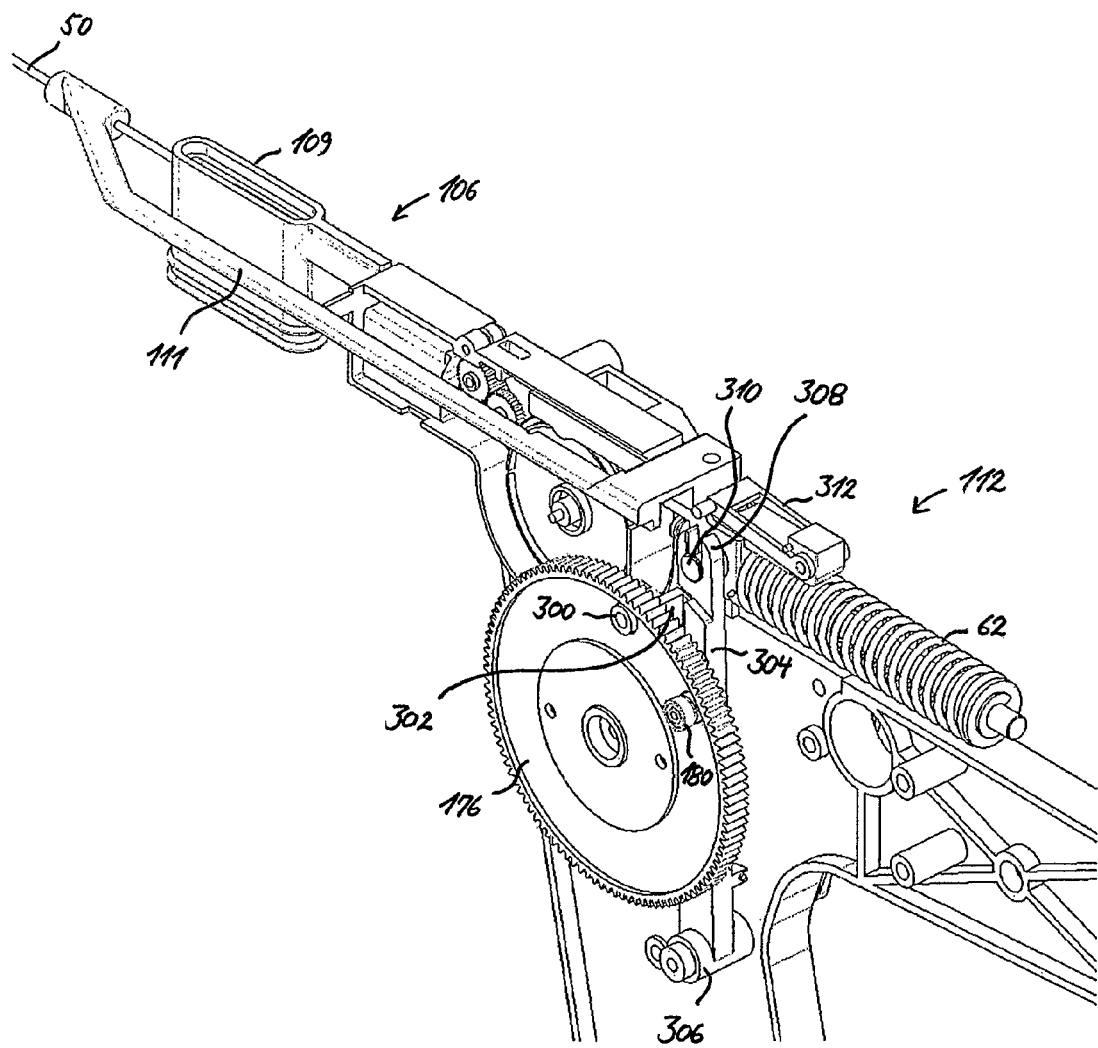

The element 312 is pivotally mounted to a sliding support member 314 secured to the compression spring 62, and it is upwardly spring-biased to the inclined position shown in FIGS. 27 and 28. The sliding support member 314 is connected to the trigger arm 304 via a connector 313 integral with the transmission element 310. When the double shot firing mechanism is to be loaded as described above in connection with FIGS. 7-26, the element 312 is kept in a substantially non-inclined position (not shown) to allow the needle driver 111 to slide past the upper surface of the element 312, the element 312 being forced into its non-inclined position by the yoke 182 (cf. e.g. FIG. 13).

Figure 29:
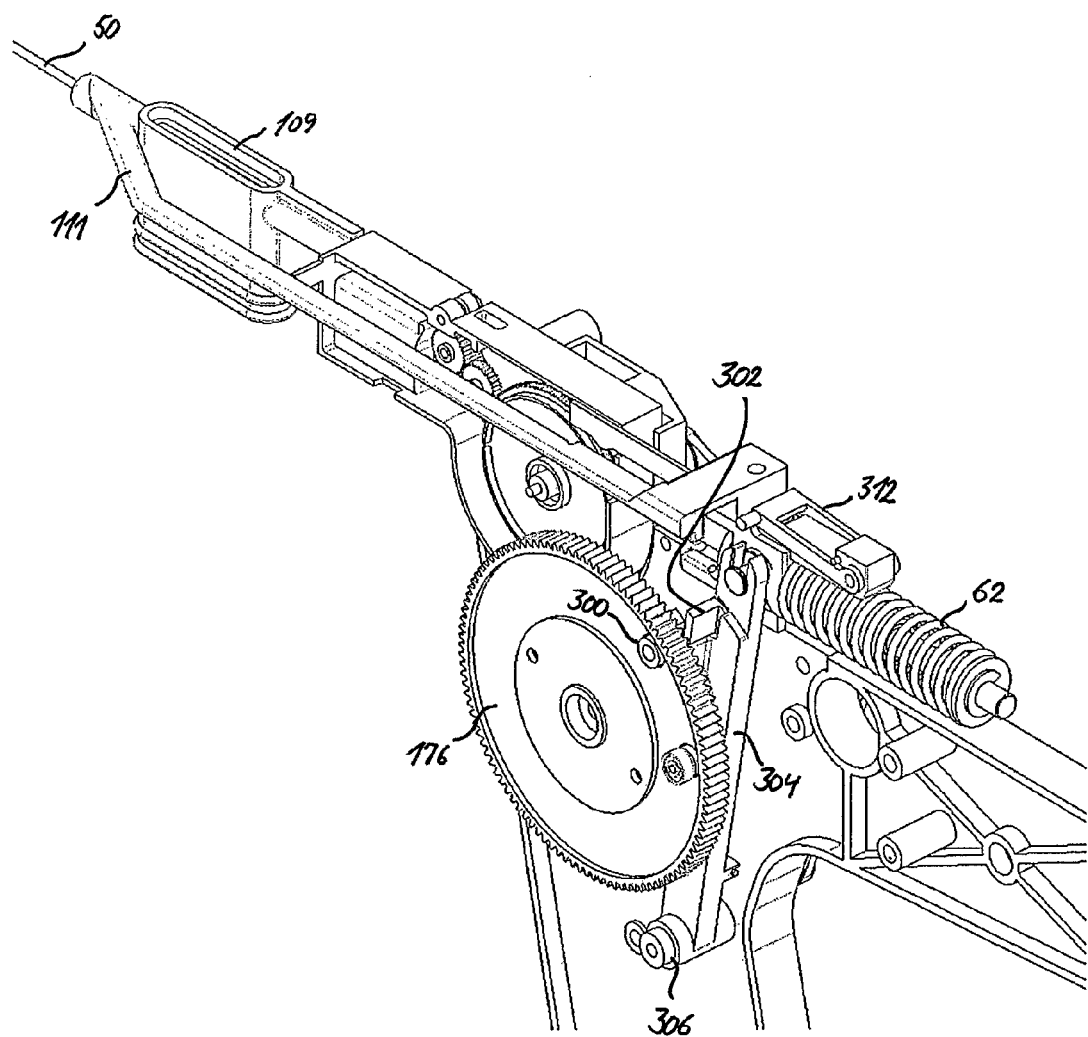
Figure 30:
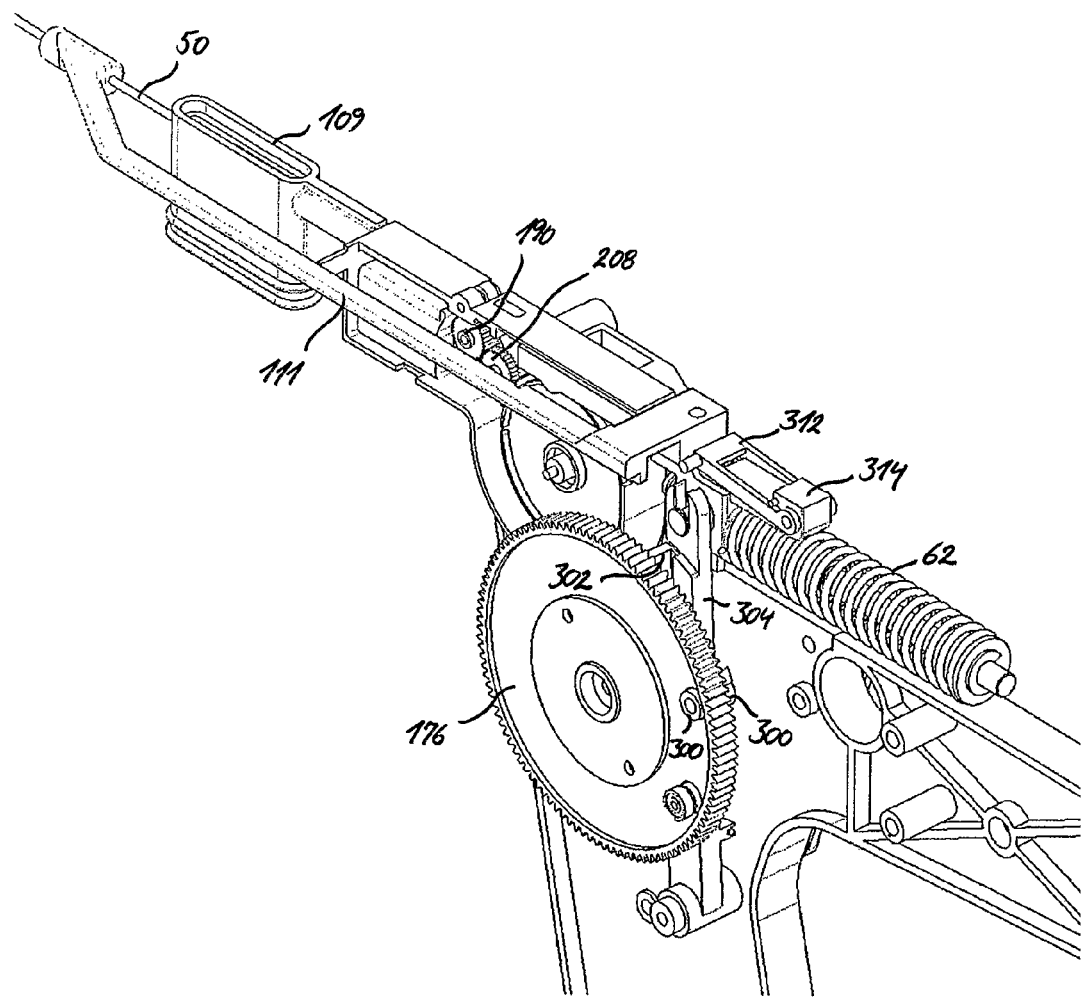

Upon further rotation of the trigger wheel 176, the trigger arm 304 is rotated around its pivot 306, as the third bearing element 300 imparts the impart cam 302 of the trigger arm 304, cf. FIG. 29. Consequently, the compression spring 62 is compressed, as a proximal end of the spring is appropriately supported. It will be appreciated that in the position of FIG. 29, the outer needle 50 has been retracted, whereby the canoe 56 of the sample-receiving device 52 (cf. FIG. 1) is laid bare distal to the distal end portion of the outer needle 50. The position of FIG. 29 thus corresponds to the position of FIG. 1. In this position, vacuum is applied to the canoe 56 via the vacuum port 58 to suck body tissue into the canoe 56. In FIG. 30, the trigger wheel 176 has rotated further to a position, in which the third bearing element 300 looses its engagement with the impart cam 302 of the trigger arm 304, and the compression spring 62 is hence unloaded, whereby the needle driver 111 is released and shot (i.e. fired) forwardly, i.e. in the distal direction. Thereby, tissue sucked into the canoe 56 (cf. FIG. 1) is severed by the circumferential cutting edge 60 of the outer needle 50, so that a severed tissue sample is now accommodated in the canoe 56.

Figure 31:
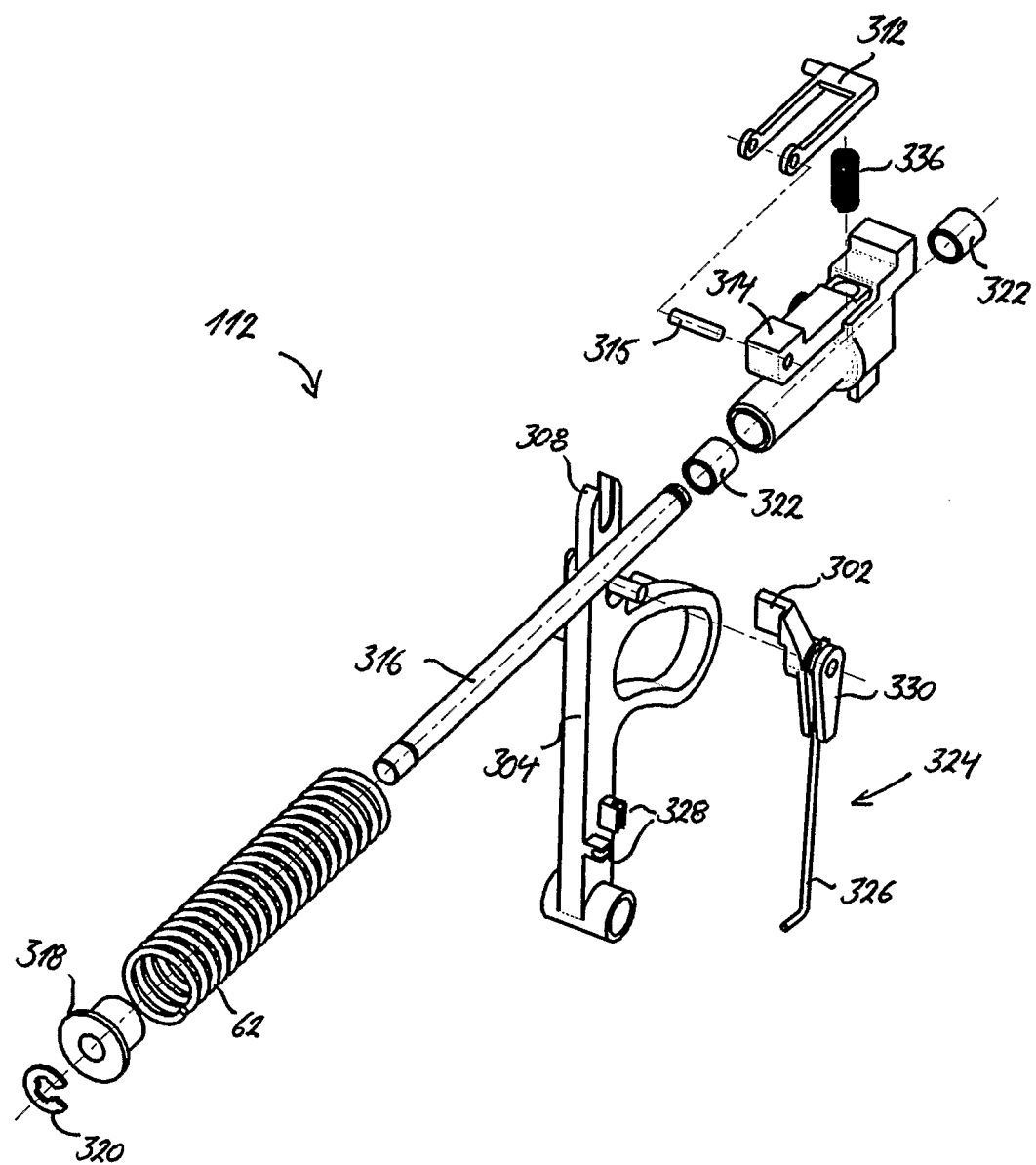

The single-shot firing mechanism 112 is further illustrated in the exploded view of FIG. 31. A supporting axle 316 extends through the compression spring 62 and is supported proximally thereof by a bushing 318 and a lock washer 320. A distal end of the supporting axle 316 extends through the sliding support member 314, in which it is supported by a pair of bushings 322. A pivot pin 315 is provided for the pivotable element 312. To ensure that the trigger arm 304 is biased in the proximal direction, a biasing mechanism 324 is mounted to the trigger arm 304 via a spring element 326, one end of which is fixed in engagement grooves 328 provided on the trigger arm 304. Another, opposite end of the spring element 326 is fixed to a gate element 330 forming the impart cam 302 (cf. FIGS. 27-29). A compression spring 336 is provided to bias the pivotable element 312 towards an upwardly inclined position, in which it is in contact with a proximal surface of the needle driver 111 (cf. FIGS. 27-30).

As described above with reference to FIGS. 27-31, rotation of the trigger wheel 176 causes loading and firing of the single-shot firing mechanism for severing a body tissue sample, which is now collected in the canoe 56 of the sample-receiving device 52 (cf. FIG. 1). Further rotation of the trigger wheel 176 causes movement of the bendable elongate element 66 (cf. FIGS. 1 and 19-23) in the proximal direction to move the canoe 56 from its first extended position, in which it is accommodated in the distal end portion of the hollow needle 50, to its second retracted position, in which it is aligned with the flushing chamber 109 (cf. e.g. FIGS. 27-30) for ejection of the body tissue sample by liquid flushing. This movement of the bendable elongate element 66 will now be further described with reference to FIGS. 32-36, showing a drive wheel 340, which forms a toothed arc portion 342 and a connecting portion 344. A free end of the connecting portion 344 is pivotally mounted to a roller 346, which may slide in a curved track 348 formed in a carrier plate 350. The drive wheel 340 is rotationally supported at a centre point 352 of the toothed arc portion 342. It will be understood from FIG. 36 that the drive wheel 340 is connected to the trigger wheel 176 via the rotational support at 352, at which the drive wheel 340 is connected to a cam washer 354 forming a notch 356 for engagement with a reduced diameter portion 347 of the roller 346. The cam washer 354 engages a circular element 358 secured to the trigger wheel 176. During rotation of the trigger wheel 176 from the initial position shown in FIG. 11 to the position shown in FIG. 30, the notch 356 is out of engagement with the roller 346, and accordingly the drive wheel 340 is not rotated. Upon further rotation of the trigger wheel 176, the notch 356 of the cam washer 354 engages the roller 346, and thereby the free end of the connecting portion 344 of the drive wheel 340 is forced downwardly in the curved track 348. This in turn causes the drive wheel 340 to rotate around its rotational support at 352, whereby the drive wheel 340 is rotated from the position of FIG. 32 to the position of FIG. 34.

Figure 32:
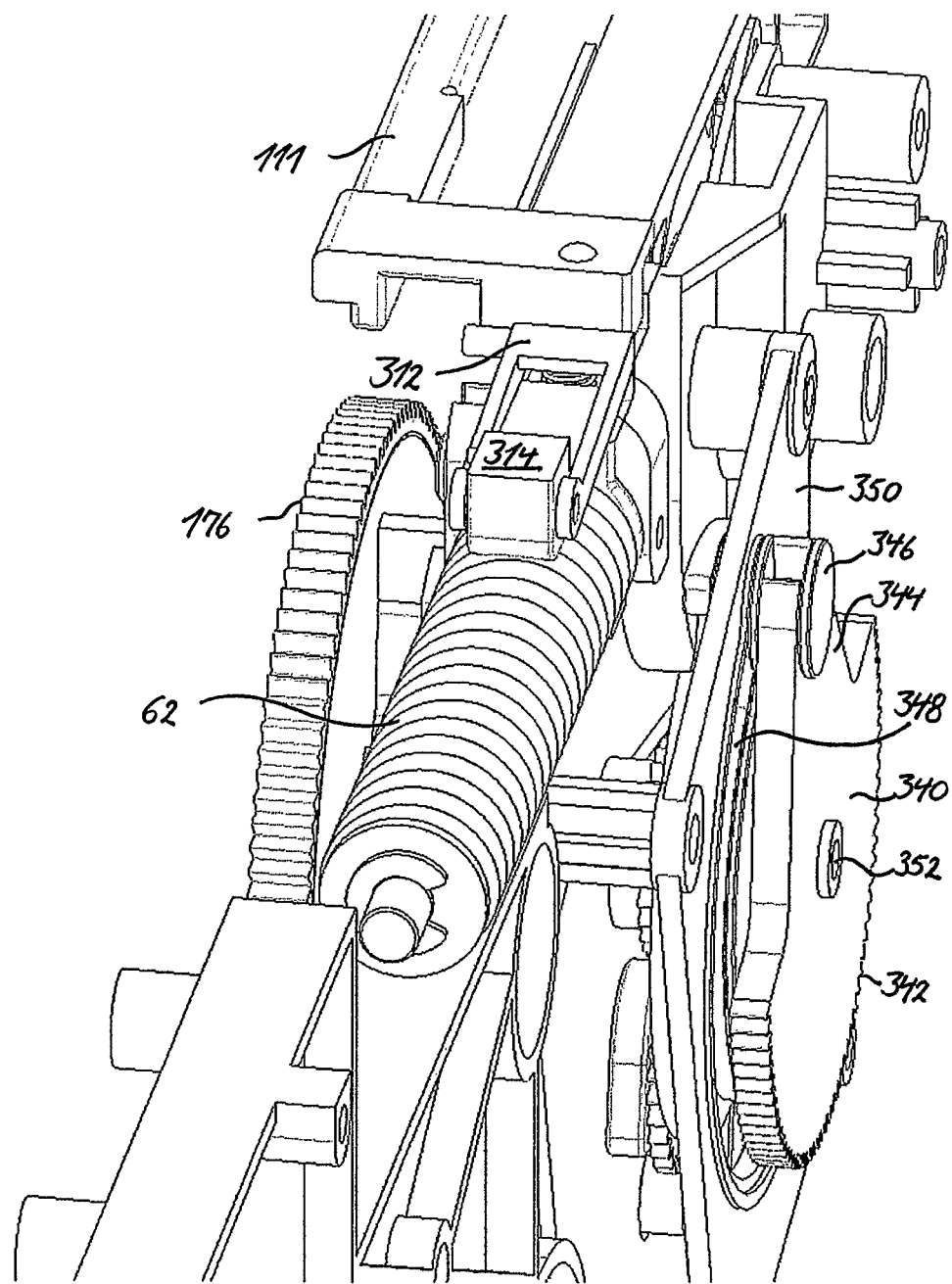
FIGS. 32-35 illustrate a mechanism for moving the sample-receiving device in the outer needle.
Figure 33:
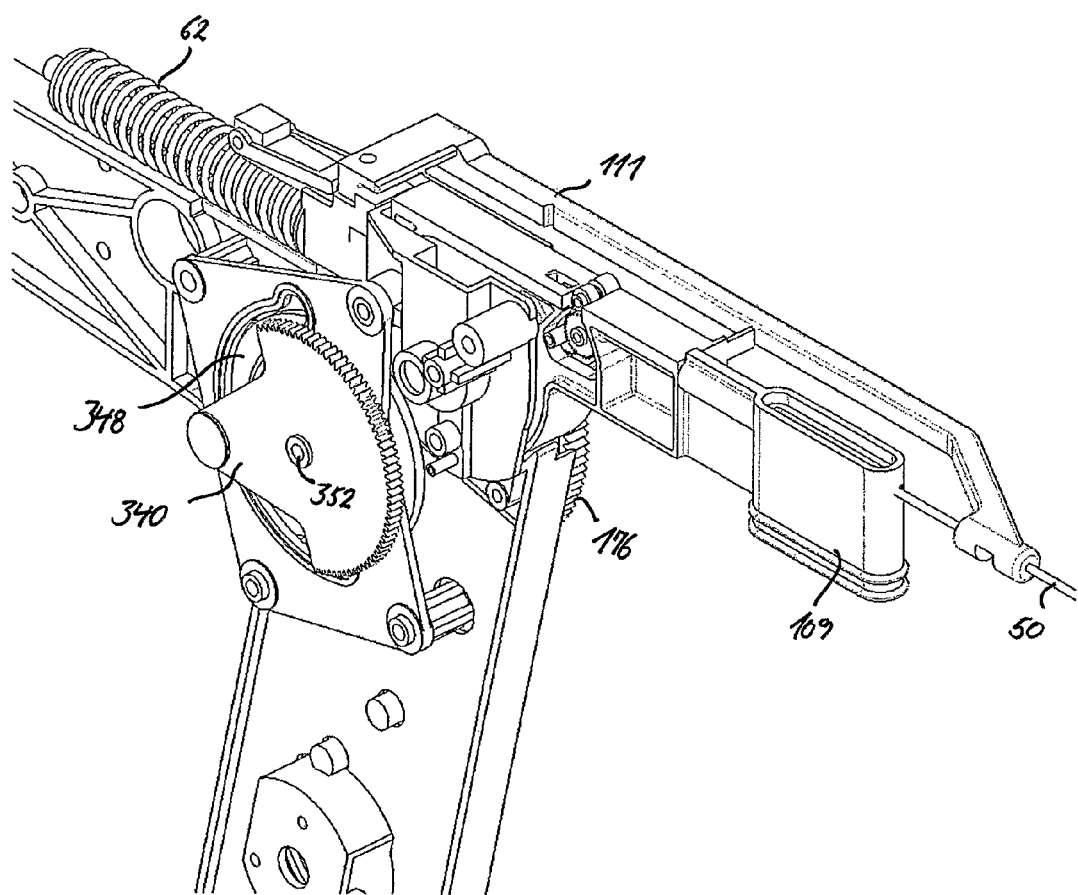
Figure 34:
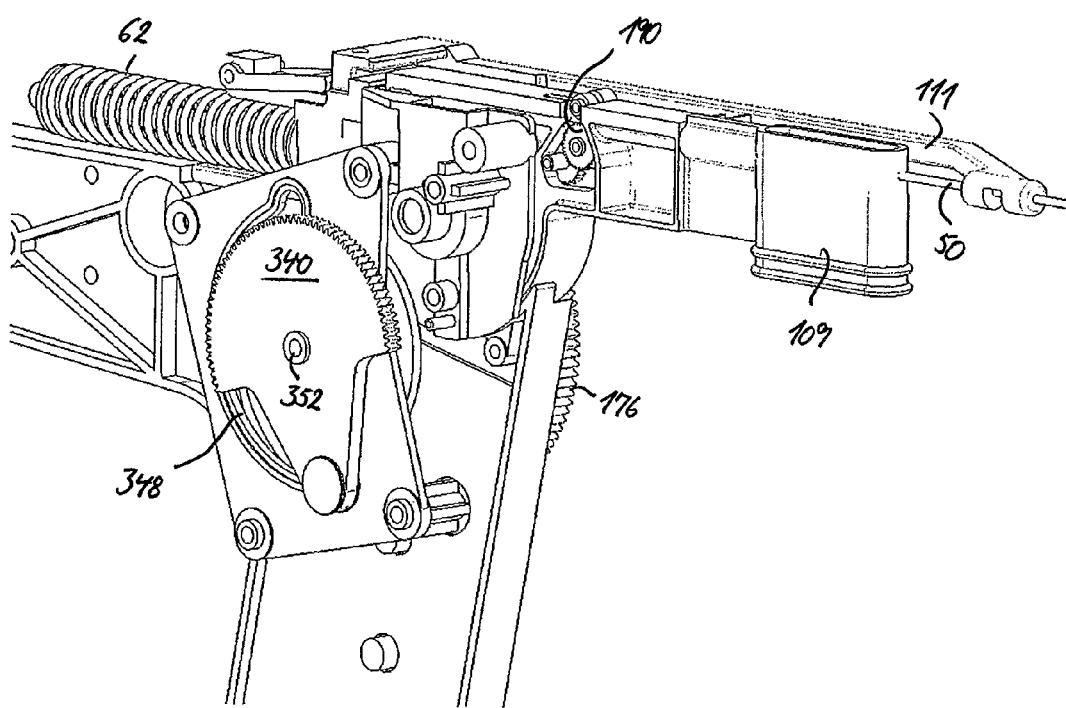
Figure 35:
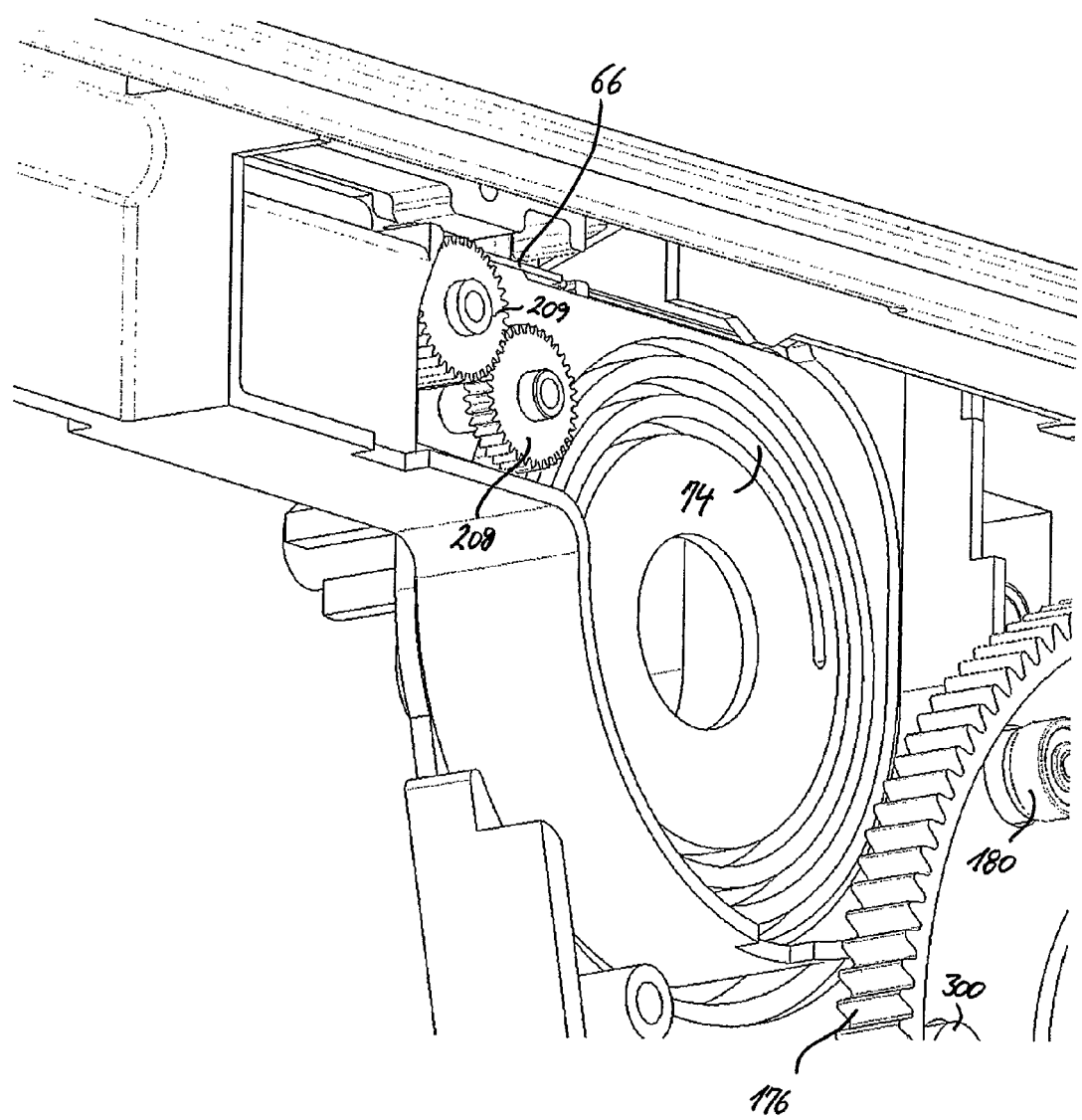

During the rotation of the drive wheel 340 as described above, the toothed arc portion 342 of the drive wheel 340 engages a gear drive, which is not shown in FIGS. 32-34. The gear drive, which is partly visible in FIG. 36, comprises a first gearwheel 360, which is engaged by the toothed arc portion 342 of the drive wheel. The first gearwheel 360 drives a second gearwheel 362. An axle 364 for the first gearwheel 360 is mounted in a first sleeve 366, and an axle 368 for the second gearwheel 362 extends through a cross-shaped reinforcement member 369 and engages a connector 370, which provides a driving force transmission interconnection to the driving gearwheel 204 (cf. FIGS. 19-23) included in the disposable unit 106 (cf. FIGS. 2 and 8). The disposable unit 206 also accommodates the bendable elongate element 66 for moving the sample-receiving device 52 in the hollow needle 50 (FIG. 2), the flushing chamber 109, and the coiling device 74 (FIG. 35) for coiling up the bendable elongate element 66. The driving gearwheel 204, which is omitted in FIG. 35 in order not to cover the coiling device 74, drives the intermediated gearwheel 208 and the advancing gearwheel 190, which in turn engages teeth of the bendable elongate element 66. When the bendable elongate element 66 is moved in the proximal direction to retract the sample-receiving device for ejection of the harvested tissue sample, the bendable elongate element is coiled into the coiling device 74 forming a spiral, which allows the bendable elongate element 66 to be wound up and unwound in a controlled manner.

Figure 36:
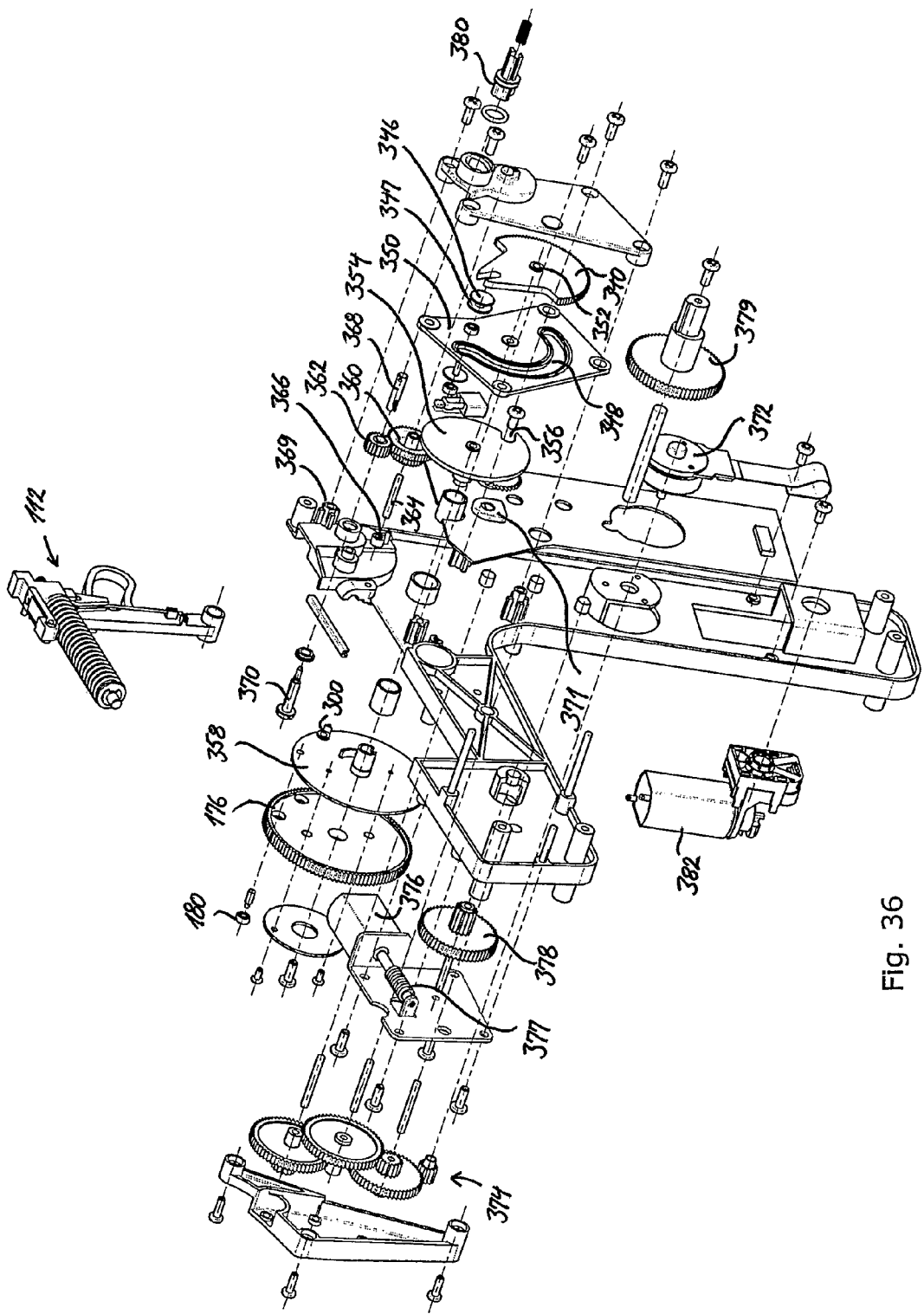
FIG. 36 is an exploded view of a gear chassis of the biopsy device.

The gear chassis 104 (cf. FIG. 2) includes further elements shown in FIG. 36. A driving motor 372 is provided for driving the trigger wheel 176 via a gear drive 374. A further motor 376 is provided for driving the peristaltic pump 118 (cf. FIGS. 2-6) for sample ejection by liquid flush via a spindle 377 and gearwheels 378 and 379. A glide bushing 380 is provided for the connector 370 to receive the disposable unit 106 in the handle unit 105 (cf. 2). A vacuum pump 382 is provided for creating vacuum suction to suck body tissue into the canoe 56 of the sample-receiving device 52 (cf. FIGS. 1 and 2), the vacuum pump 382 being in fluid communication with the canoe 56 via appropriate tubes (not shown) and the vacuum port 58.

Figure 37:
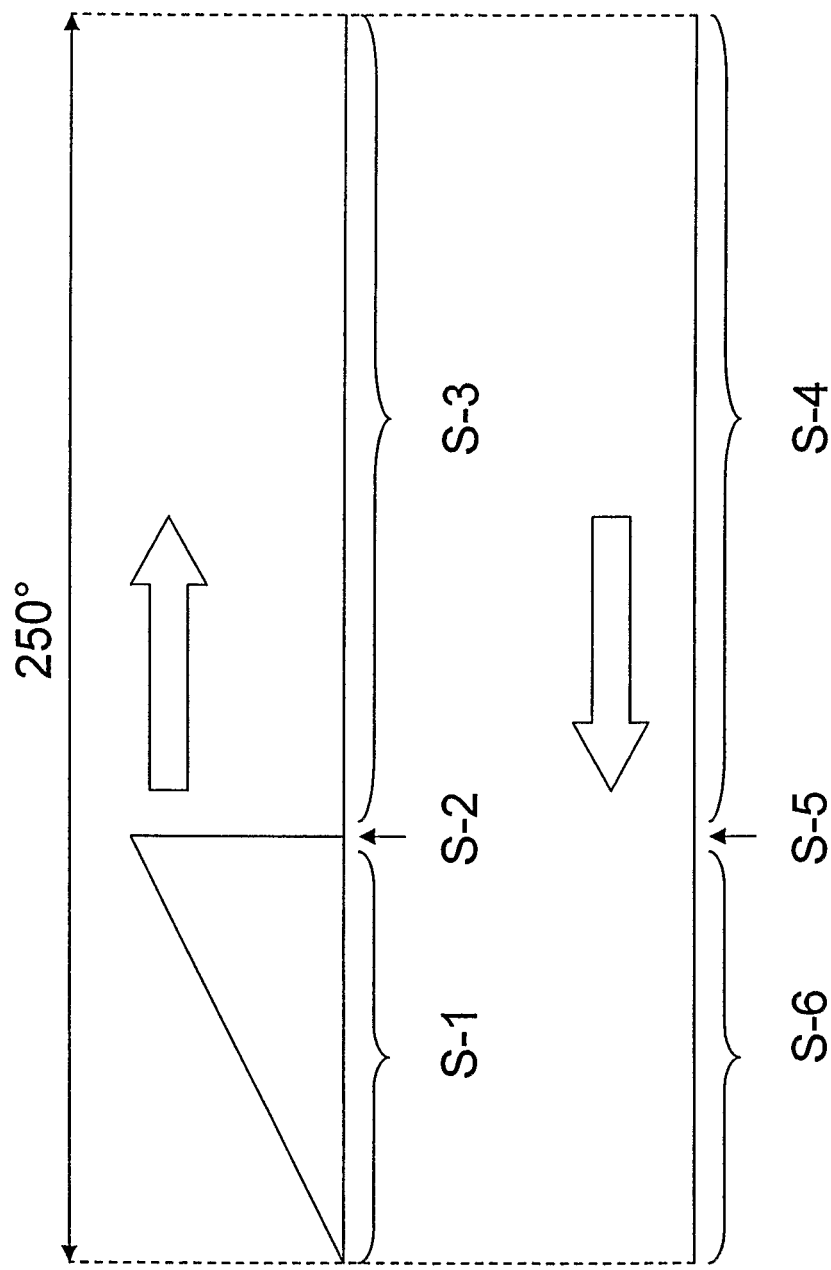
FIGS. 37 and 38 illustrate cycles of a trigger wheel of the first and second firing mechanisms.
Figure 38:
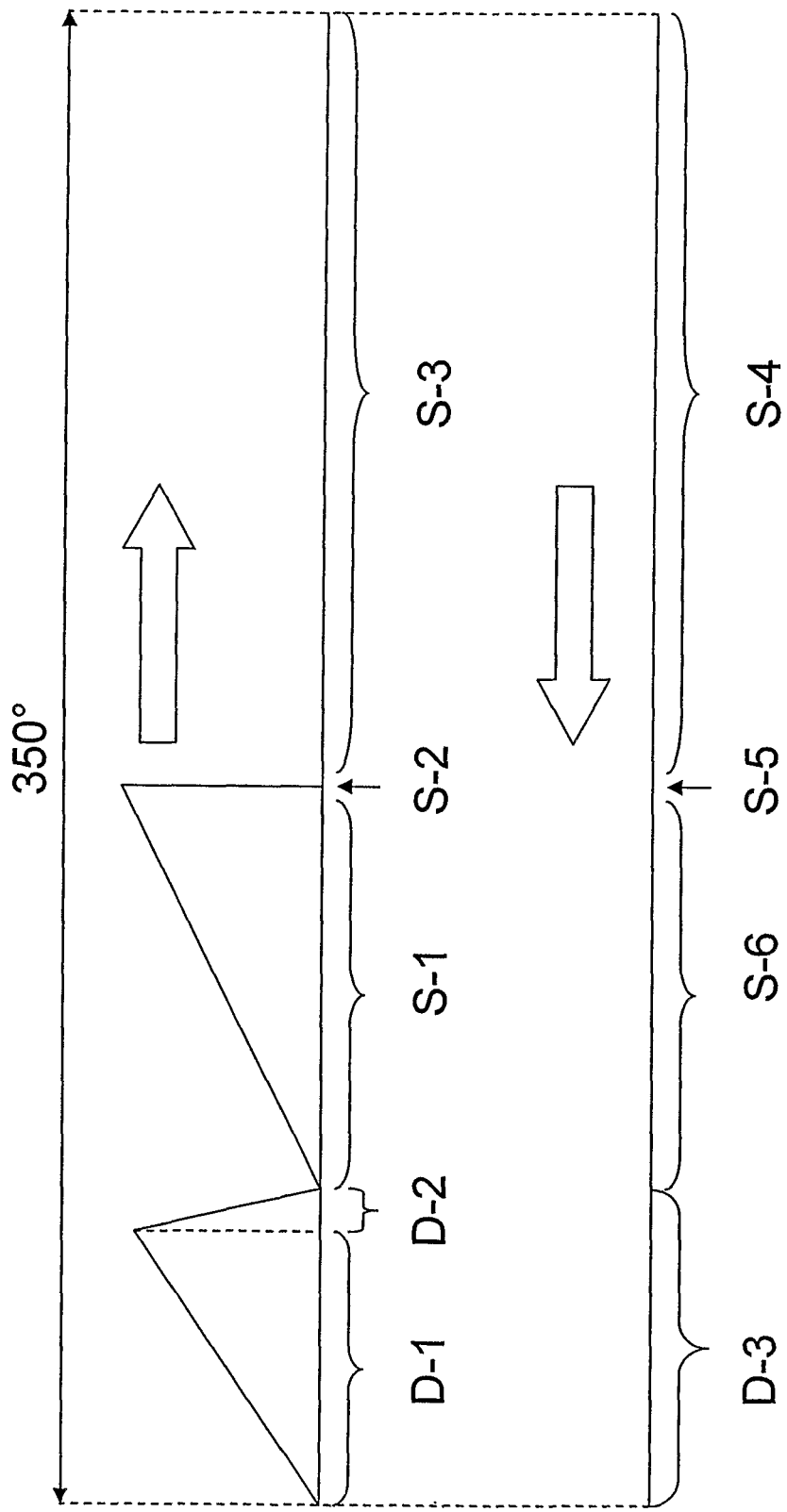

The cycle of the trigger wheel 176 described above with reference to FIGS. 9-17 and 27-35 regarding double- and single shot, respectively, is diagrammatically illustrated in FIGS. 37 and 38. FIG. 37 shows the cycle of the movement of the trigger wheel described in relation to FIGS. 28-34 and back. From the position of FIG. 28, the trigger wheel rotates approximately 290° to the position of FIG. 34. During a first segment of the rotation, S-1, corresponding to the rotation of the trigger wheel 176 from the position of FIG. 28 to the position of FIG. 29, the compression spring 62 is compressed. At S-2, the third bearing element 300 looses contact with the upright impart cam 302, thereby unloading the spring 62. The trigger wheel 176 has now rotated the cam washer 354 (cf. FIG. 36) to the position, in which the notch 356 engages the roller 346. During a subsequent segment of the rotation, S-3, the trigger wheel 176 rotates further to move the drive wheel 340 from the position of FIG. 32 to the position of FIG. 34 to thereby pull the sample-receiving device 52 backwards to its second retracted position, in which the canoe 56 is aligned with the flushing chamber 109 for ejection of the severed tissue sample collected in the canoe 56. Rotation of the trigger wheel 176 is now reversed, as indicated by block arrows in FIG. 37. During that segment of the reverse rotation, which is denoted S-4 in FIG. 37, the trigger wheel 176 moves the drive wheel 340 back from the position of FIG. 34 to the position of FIG. 32 to thereby move the sample-receiving device 52 to the distal end portion of the outer needle 50, i.e. to the first extended position of the sample-receiving device. At S-5, the sample-receiving device 52 is now at its distal extremity, and the notch 356 of the cam washer 354 (cf. FIG. 36) disengages the roller 346. A final segment of the reverse rotation of the trigger wheel 176, S-6, is an idle run, in which the trigger wheel 176 is moved from a position approximately equal to the position of FIG. 40 to the position of FIG. 28. Immediately prior to the termination of the S-6 rotation, the third bearing element 300 contacts and passes the impart cam 302, which is biased in the proximal direction by the spring element 326 (cf. FIG. 31). If a further tissue sample is to be severed, the above cycle may now be repeated.

In FIG. 38, that segment of the rotation of the trigger wheel 176, which causes the double shot described above with reference to FIGS. 9-17, is added to the S-1-S-6 rotation segments shown in FIG. 37. During a first rotation segment D-1, the trigger wheel 176 is rotated from the position of FIG. 11 to the position of FIG. 12 to compress the compression spring 138 (cf. e.g. FIG. 12). Upon further rotation, D-2, the compression spring 138 is unloaded to substantially simultaneously fire the outer needle 50 and the sample-receiving device 52, i.e. to move the trigger wheel from the position of FIG. 16 to the position of FIG. 17. The S-1-S-6 rotation segments are now performed as described above with reference to FIG. 37. During a final reverse rotation segment, D-3, the trigger wheel 176 is rotated from a position, which is slightly upstream of the position depicted in FIG. 12 (the trigger wheel rotating counterclockwise in FIG. 12), to the position of FIG. 11. As the solenoid 148 (cf. FIGS. 9 and 10) is deactivated, so that the double shot lever 156 is biased to its inclined position of FIG. 9, the impart member 170 is not in the plane of the first bearing element 180 (cf. FIGS. 11 and 12), so that bearing element 180 may pass freely to the position of FIG. 11 without contacting the impart member 170.

In one embodiment of the invention, the control system of the biopsy device is configured such that a double shot sequence is automatically followed by a single-shot sequence. In other embodiments, the double shot may be activated without incurring a single-shot sequence.

It will be appreciated that the operation of the device, including activation of the double- and single-shot sequences described above with reference to FIGS. 9-35, and activation of ejection flushing, may be controlled by an operator via an appropriate touch-pad system provided e.g. on an exterior surface of the handle unit 105 (cf. FIG. 2).

In the embodiment described above with reference to FIGS. 1-38, controlling of the movement of the needle 50 and the sample-receiving device 52 is widely based on mechanical means, except for certain electronically controlled elements, such as the solenoid 148 (cf. e.g. FIGS. 9 and 10), the motor 372, vacuum pump 382 (FIG. 36) and the peristaltic pump 118 for liquid flushing for tissue sample ejection. It should, however, be understood that the control system may incorporate further electronic elements. For example, the double- and single shot firing mechanisms may be driven by separate motors, which are electronically controlled, and loading and firing of the first and second mechanisms for single and double shot, respectively, may incorporate electronically controlled elements for causing appropriate engagement and disengagement of various parts.

Figure 39:
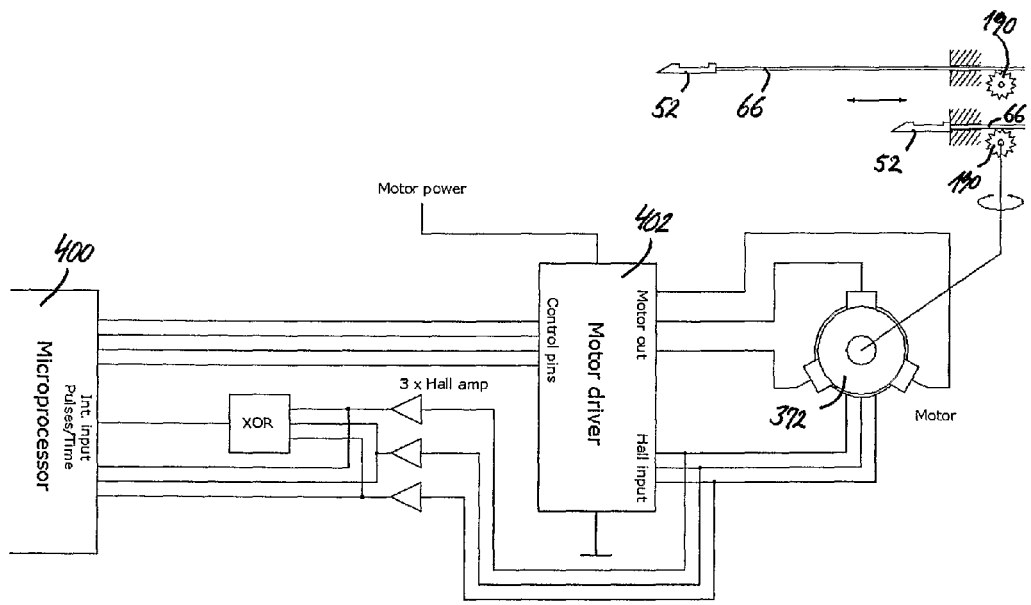
FIGS. 39 and 40 illustrate an embodiment of a system for determining a distance between two positions of the sample-receiving device.
Figure 40:
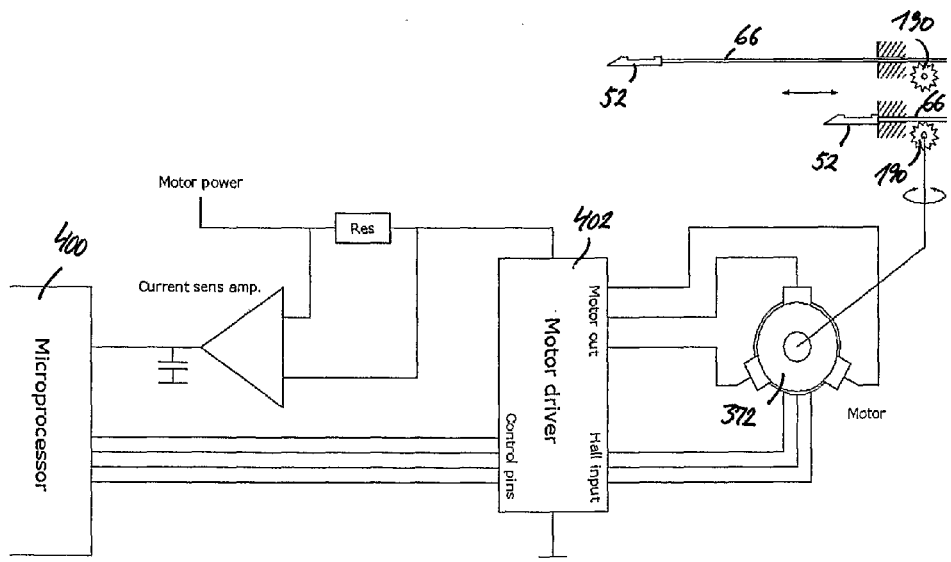

FIGS. 39 and 40 illustrate two alternative embodiments of the control system for determining the distance between the first extended position of the sample-receiving device 52 and its second retracted position, e.g. to provide automatic detection of the length of the outer hollow needle 50.

The control system uses a microcontroller 400 to constantly monitor the rotation of the motor unit 372 of the handle unit 105. Simultaneously herewith, the system monitors, by means of an appropriate position sensor 371 (cf. FIG. 36) the position of one of the transmission axles that are part of the gear system translating the movement from the motor unit to the bendable elongate element 66. Thus, the position of the bendable elongate element may be known at all times, and the system may configure itself according to the length of the bendable elongate element, and thus to the length of the outer needle 50 (cf. e.g. FIG. 2).

The embodiment in FIGS. 39 and 40 includes three sensors that are connected directly to the motor unit 372 in the handle unit 105, and which record the rotation of the motor, cf. FIG. 39. These sensors may be of the Hall sensor type or of a similar type, and their output is fed into a motor driver unit 402 and a microprocessor 400. When the motor unit 372 is activated and starts rotating, movement is translated from the motor to the bendable elongate element 66. As long as the bendable elongate element is free to move within the lumen of the outer hollow needle 50, a steady stream of pulses are fed from the Hall sensors to the motor driver 402 and the microprocessor 400. When the bendable elongate element reaches the end of its movement spectrum, it arrests the motion of the motor 372 and breaks the steady stream of pulses from the sensors. This cease of impulses is recorded by the microprocessor 400.

As an additional measure, the microprocessor 400 may record the position of the aforementioned transmission axle. Information about the position of the transmission axle may be provided by a potentiometer mounted on the transmission axle. A DC signal obtained from a wiper of the potentiometer may reflect the instantaneous position of the transmission axle and the entire movement spectrum of the bendable elongate element 66 corresponding to an angle of rotation of 300 degrees. Since the position of the axle when the bendable elongate element 66 reaches its second retracted position is recorded—and may be found again by means of the output from the potentiometer—the microprocessor 400 may reduce the wear on the motor by gradually reducing its speed and stopping it immediately prior to reaching the position corresponding to the second retracted position of the bendable elongate element 66.

An alternative or complement to measuring the rotation of the motor 372 directly is to measure motor current passing through the motor. Results of this measurement may be transmitted to a microcontroller or microprocessor wherein a suitable microprocessor program or software comprises a pre-defined current threshold. This measurement of motor current may be done with a sampling A/D converter integrated with the microcontroller or a corresponding external device. As long as the bendable elongate element 66 is free to move within the lumen of the outer hollow needle 50, the load on the motor is substantially constant, and thus the motor current is also constant. When the load increases because the rod or rack has reached either end of its movement spectrum, the motor current increases. When the current reaches a pre-defined threshold value, the current change is recorded by a motor driver unit that is an integrated part of the control system. Simultaneously, the microcontroller may record the position of the transmission axle. Information about the position of the transmission axle may be provided by a suitable electrical or optical signal derived from e.g. a potentiometer.

A third means of transmitting information about the length of the bendable elongate element 66 to the microcontroller is to use a mechanical means, such as a spring-loaded pin that slides into a recess in the bendable elongate element 66 or the sample-receiving device 52. Also optomechanical means may be utilized.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

The invention claimed is:

1. A biopsy device for harvesting at least one tissue sample from a body of a living being, the device comprising:
    a hollow needle with a distal end portion having a cutting mechanism for severing the at least one tissue sample;
    a sample-receiving device with a cavity for receiving the at least one severed tissue sample, the sample-receiving device being received in the hollow needle and movable in the hollow needle;
    a drive mechanism configured to displace the hollow needle in a distal direction relative to the sample-receiving device to sever tissue received in the cavity of the sample-receiving device;
    a transport device including a bendable elongate element that is coupled to the sample-receiving device to move the sample-receiving device in the hollow needle, wherein the bendable elongate element is bendable away from the longitudinal direction of the hollow needle; and
    a spiral-shaped wall arranged at a proximal end of the transport device, the spiral-shaped wall defines a spiral-shaped cavity, the spiral-shaped cavity configured to receive the bendable elongate element as the sample-receiving device is retracted through the hollow needle so that each successive winding of the bendable elongate element is separated from one another.

2. A biopsy device according to claim 1, wherein the hollow needle, the spiral-shaped wall, and the sample-receiving device form a disposable unit.

3. A biopsy device according to claim 1, wherein the sample-receiving device is movable in the hollow needle between a first extended position and a second retracted position, wherein at the first extended position the cavity of the sample-receiving device is distal to the distal end of the hollow needle to facilitate severance of the at least one tissue sample by the cutting mechanism, and wherein at the second retracted position the cavity of the sample-receiving device is within the hollow needle.

4. A biopsy device of claim 1, wherein:
    a sample retrieval location is located proximal to the proximal end of the hollow needle;
    the sample-receiving device is movable between a first extended position and a second retracted position, wherein at the first extended position the sample-receiving device extends through the hollow needle so that the cavity of the sample-receiving device is distal to the distal end of the hollow needle to facilitate severance of the at least one tissue sample by the cutting mechanism, and wherein at the second retracted position the cavity of the sample-receiving device is positioned at the sample retrieval location; and
    said transport device being further configured to retract the sample-receiving device through the hollow needle from the first extended position to the second retracted position while the hollow needle is displaced in the distal direction so as to position the cavity at the sample retrieval location within the biopsy device to facilitate delivery of the tissue sample to a sample container.

5. A biopsy device for harvesting at least one tissue sample from a body of a living being, the device comprising:
- a hollow needle with a distal end portion having a cutting mechanism for severing the at least one tissue sample;
- a sample-receiving device with a cavity for receiving the at least one severed tissue sample, the sample-receiving device being received in the hollow needle and movable in the hollow needle;
- a drive mechanism configured to displace the hollow needle in a distal direction relative to the sample-receiving device to sever tissue received in the cavity of the sample-receiving device;
- a transport device including a toothed flexible rack and a rotatable gear wheel, the toothed flexible rack coupled to the sample-receiving device to facilitate movement of the sample-receiving device in the hollow needle; and
- a spiral wall arranged at a proximal end of the transport device, the spiral wall defining a spiral cavity configured to receive the toothed flexible rack as the sample-receiving device is retracted through the hollow needle so that each successive winding of the toothed flexible rack is separated from one another;
- wherein the toothed flexible rack has a row of regularly spaced teeth, and the rotatable gear wheel has a rim with teeth configured to mesh with the teeth of the toothed flexible rack so as to move the toothed flexible rack and the sample-receiving device in the hollow needle when the transport device is operated.

6. A biopsy device according to claim 5, wherein the cutting mechanism comprises a circumferential cutting edge.

7. A biopsy device according to claim 6, wherein the sample-receiving device is movable in the hollow needle between a first extended position and a second retracted position, wherein at the first extended position the cavity of the sample-receiving device is distal to the distal end of the hollow needle to facilitate severance of the at least one tissue sample by the cutting mechanism, and wherein at the second retracted position the cavity of the sample-receiving device is within the hollow needle.

8. A biopsy device according to claim 7, wherein:
- the drive mechanism is further configured to displace the hollow needle in the distal direction relative to the sample-receiving device such that the sample-receiving device is in the first extended position prior to the displacement of the hollow needle and is in the second retracted position after the displacement of the hollow needle;
- the toothed flexible rack is configured to move the sample-receiving device between the first extended position and the second retracted position; and
- the spiral cavity is configured to receive the toothed flexible rack as the sample-receiving device is retracted through the hollow needle from the first extended position to the second retracted position.

9. A biopsy device according to claim 5, wherein the sample-receiving device has a length which is shorter than a length of the hollow needle.

10. A biopsy device according to claim 5, further comprising a handle unit with a power source and a motor for driving the transport device, and wherein the transport device, the hollow needle and the sample-receiving device are comprised in a disposable unit, which is releasably secured to the handle unit.

11. A biopsy device according to claim 10, wherein the handle unit and the disposable unit are configured to be handheld when secured to each other.

12. A disposable unit for harvesting at least one tissue sample from a body of a living being and for releasable connection to an external unit of a biopsy device the disposable unit comprising:
- a hollow needle with a distal end portion having a cutting mechanism configured to sever the at least one tissue sample;
- a sample-receiving device with a cavity for receiving the at least one severed tissue sample, the sample-receiving device being received in the hollow needle and movable in the hollow needle;
- a transport device coupled to the sample-receiving device and configured to move the sample-receiving device in the hollow needle, the transport device including a flexible elongate element that is configured to flex into a curved configuration when retracted;
- a spiral wall arranged at a proximal end of the transport device, the spiral wall being configured to define a spiral path that receives the flexible elongate element as the sample-receiving device is retracted so that each successive winding of the flexible elongate element is spaced apart from one another; and
- an interface configured for connecting the disposable unit to the external unit, and the interface being further configured to transmit a driving force of the external unit to the transport device.

13. A disposable unit for harvesting at least one tissue sample from a body of a living being and for releasable connection to an external unit of a biopsy device the disposable unit comprising:
- a hollow needle with a distal end portion having a cutting mechanism configured to sever the at least one tissue sample;
- a sample-receiving device with a cavity for receiving the at least one severed tissue sample, the sample-receiving device being received in the hollow needle and movable in the hollow needle;
- a transport device including a bendable elongate element coupled to the sample-receiving device, the transport device being configured to move the sample-receiving device in the hollow needle;
- a coiling device configured for coiling up the bendable elongate element as the sample-receiving device is retracted by the transport device, the coiling device comprising a spiral wall arranged at a proximal end of the transport device, the spiral wall being configured to define a spiral path that receives the bendable elongate element as the sample-receiving device is retracted so that each successive winding of the bendable elongate element is separated from one another; and
- an interface configured for connecting the disposable unit to the external unit, and the interface being further configured to transmit a driving force of the external unit to the transport device.

14. A biopsy device according to claim 13, wherein the sample-receiving device is movable in the hollow needle between a first extended position and a second retracted position, wherein at the first extended position the cavity of the sample-receiving device is distal to the distal end of the hollow needle to facilitate severance of the at least one tissue sample by the cutting mechanism, and wherein at the second retracted position the cavity of the sample-receiving device is within the hollow needle.

15. A biopsy device for harvesting at least one tissue sample from a body of a living being the device comprising:
- a hollow needle with a distal end portion having a cutting mechanism for severing the at least one tissue sample;

a sample-receiving device with a cavity for receiving the at least one severed tissue sample, the sample-receiving device being received in the hollow needle and movable in the hollow needle;

a drive mechanism configured to displace the hollow needle in a distal direction relative to the sample-receiving device to sever tissue received in the cavity of the sample-receiving device;

a transport device including a flexible elongate element that is coupled to the sample-receiving device to move the sample-receiving device in the hollow needle between the first extended position and the second retracted position; and a spiral-shaped wall arranged at a proximal end of the transport device, the spiral-shaped wall defines a spiral-shaped cavity, the spiral-shaped cavity configured to receive the flexible elongate element as the sample-receiving device is retracted through the hollow needle, and the spiral-shaped cavity is further configured to prevent the received portion of the flexible elongate element from contacting successive windings of the flexible elongate element.

16. The biopsy device of claim 15, wherein:

a sample retrieval location is located proximal to the proximal end of the hollow needle;

the sample-receiving device is movable between a first extended position and a second retracted position, wherein at the first extended position the sample receiving device extends through the hollow needle so that the cavity of the sample-receiving device is distal to the distal end of the hollow needle to facilitate severance of the at least one tissue sample by the cutting mechanism, and wherein at the second retracted position the cavity of the sample-receiving device is positioned at the sample retrieval location; and said transport device being further configured to retract the sample-receiving device through the hollow needle from the first extended position to the second retracted position while the hollow needle is displaced in the distal direction so as to position the cavity at the sample retrieval location within the biopsy device to facilitate delivery of the tissue sample to a sample container.

17. A biopsy device according to claim 16, further comprising a liquid supply unit adapted to carry a flushing liquid, the liquid supply unit having a sample flushing chamber that is located at the sample retrieval location and is aligned in fluid communication with the cavity of the sample-receiving device when the sample-receiving device is positioned in the second retracted position, the liquid supply unit configured to facilitate ejection of the tissue sample from the cavity by liquid flushing when the sample-receiving device is positioned in the second retracted position.

18. The biopsy device of claim 15, further comprising a swivel coupling interposed between the flexible elongate element and the sample-receiving device.

19. A biopsy device according to claim 15, wherein the cavity in the sample-receiving device has a lateral opening.

20. A biopsy device according to claim 15, wherein the flexible elongate element is configured to flex away from the longitudinal direction of the hollow needle.

21. A biopsy device according to claim 15, wherein the flexible elongate element comprises a steel wire.

22. A biopsy device according to claim 21, wherein the steel wire comprises two or more twisted wires.

23. A biopsy device according to claim 15, wherein the flexible elongate element has a longitudinally extending portion of noncircular cross section.

24. A biopsy device according to claim 15, wherein the sample-receiving device is movable in the hollow needle along an axis of movement, and wherein at least one of the hollow needle and the sample-receiving device is configured to orient the sample-receiving device relative to the hollow needle in a plane perpendicular to the axis of movement.

25. A biopsy device according to claim 15, wherein the sample-receiving device and the hollow needle are arranged along an axis of movement and are shaped so that relative rotational displacement between the sample-receiving device and the hollow needle in a plane perpendicular to the axis of movement is prevented.

26. A biopsy device according to claim 15, further comprising a vacuum pump for generating suction in the cavity of the sample-receiving device, the vacuum pump being in fluid communication with the cavity of the sample-receiving device through a longitudinally extending passage in the sample-receiving device.

* * * * *